United States Patent
Dai et al.

(10) Patent No.: US 10,144,700 B2
(45) Date of Patent: *Dec. 4, 2018

(54) ADENYLYL CYCLASE INHIBITORS FOR NEUROPATHIC AND INFLAMMATORY PAIN

(71) Applicant: Purdue Research Foundation, West Lafayette, IN (US)

(72) Inventors: Mingji Dai, West Lafayette, IN (US); Val J. Watts, West Lafayette, IN (US); Zhishi Ye, Dalian (CN)

(73) Assignee: PURDUE RESEARCH FOUNDATION, West Lafayette, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/920,654

(22) Filed: Mar. 14, 2018

(65) Prior Publication Data

US 2018/0230080 A1    Aug. 16, 2018

Related U.S. Application Data

(63) Continuation of application No. 15/044,660, filed on Feb. 16, 2016.

(60) Provisional application No. 62/116,686, filed on Feb. 16, 2015.

(51) Int. Cl.

| | | |
|---|---|---|
| *C07C 211/28* | (2006.01) |
| *C07D 209/14* | (2006.01) |
| *C07C 229/34* | (2006.01) |
| *C07C 229/38* | (2006.01) |
| *C07C 211/30* | (2006.01) |
| *C07C 217/62* | (2006.01) |
| *C07C 211/45* | (2006.01) |
| *C07D 295/03* | (2006.01) |
| *C07C 211/27* | (2006.01) |
| *C07C 215/34* | (2006.01) |
| *C07D 471/04* | (2006.01) |
| *C07C 239/20* | (2006.01) |
| *C07C 211/55* | (2006.01) |
| *C07C 311/16* | (2006.01) |
| *C07D 223/16* | (2006.01) |
| *C07C 229/14* | (2006.01) |
| *C07C 233/05* | (2006.01) |

(52) U.S. Cl.
CPC .......... *C07C 211/28* (2013.01); *C07C 211/27* (2013.01); *C07C 211/30* (2013.01); *C07C 211/45* (2013.01); *C07C 211/55* (2013.01); *C07C 215/34* (2013.01); *C07C 217/62* (2013.01); *C07C 229/14* (2013.01); *C07C 229/34* (2013.01); *C07C 229/38* (2013.01); *C07C 233/05* (2013.01); *C07C 239/20* (2013.01); *C07C 311/16* (2013.01); *C07D 209/14* (2013.01); *C07D 223/16* (2013.01); *C07D 295/03* (2013.01); *C07D 471/04* (2013.01)

(58) Field of Classification Search
None
See application file for complete search history.

(56) References Cited

PUBLICATIONS

Ye et al., Palladium-Catalyzed Regio- and Stereoselective γ-Arylation of Tertiary Allylic Amines: Identification of Potent Adenylyl Cyclase Inhibitors. Organic Letters, 2015, 17, 892-895.*

* cited by examiner

*Primary Examiner* — Po-Chih Chen
(74) *Attorney, Agent, or Firm* — Purdue Research Foundation; Zhigang Rao

(57) ABSTRACT

The invention generally relates to adenylyl cyclase inhibitor compounds and methods for treating neuropathic or inflammatory pain by using those compounds.

3 Claims, No Drawings

ADENYLYL CYCLASE INHIBITORS FOR NEUROPATHIC AND INFLAMMATORY PAIN

RELATED APPLICATIONS

This application is a continuation of U.S. patent application Ser. No. 15/044,660 filed Feb. 16, 2016, which claims the benefit of and priority to U.S. Provisional Application No. 62/116,686, filed Feb. 16, 2015, which is incorporated by reference herein in its entirety.

FIELD OF THE INVENTION

The invention generally relates to adenylyl cyclase inhibitors and methods of use thereof.

BACKGROUND

Adenylyl cyclases are important mediators of signaling through G protein-coupled receptors. Adenylyl cyclase type 1 (AC1) belongs to a family of adenylyl cyclases that are stimulated by calcium in a calmodulin-dependent manner. Notably, AC1 is associated with chronic pain responses in several regions of the central nervous system. Accordingly, inhibition of AC1 has resulted in analgesic effects in both neuroinflammatory and neuropathic pain in rodent models. A dearth of AC1 inhibiting compounds and an inability to efficiently synthesize them means that their analgesic benefits cannot be widely realized and people continue to suffer from neuropathic and inflammatory pain.

SUMMARY

The invention generally relates to potent adenylyl cyclase inhibitor compounds. The invention further relates to methods for treating neuropathic or inflammatory pain by delivering adenylyl cyclase inhibitor compounds of the invention. Methods of the invention also provide for palladium-catalyzed γ-arylation of tertiary allylic amines and the synthesis of the disclosed AC1 inhibitor compounds as well as drug molecules such as naftifine, cinarizine, flunarizine, and analogs thereof. Heck arylation methods of the invention provide increased regio- and stereo-selectivity and yield over known methods.

In certain aspects, the invention provides a compound of formula (I):

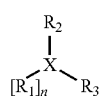

wherein: X is carbon or nitrogen; n is 0 or 1; $R_1$ is selected from aryl, alkenyl, or alkyl optionally substituted by: aryl optionally substituted by halo, fused cycloalkenyl optionally substituted by halo, or fused heterocycloalkenyl optionally substituted at the heteroatom by alkyl. $R_2$ is selected from Ts, Ac, aryl, or a branched or unbranched alkyl optionally substituted at one or more positions by $COOR_3$, aryl optionally substituted by halo, $NO_2$, alkoxy, fused heterocycloalkenyl optionally substituted by halo, $NO_2$, or alkoxy, or fused heterocycloalkenyl optionally substituted at the heteroatom by alkyl. $R_1$ and $R_2$ may be taken together with X when X is N to form a heterocycloalkyl optionally substituted at the heteroatom by $SO_2R_5$, fused heterocycloalkyl-aryl optionally substituted on the aryl ring by alkyl, Ts, or alkoxy, or $R_1$ and $R_2$ taken together with X when X is N to form the following structure:

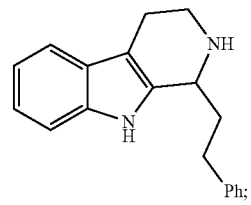 [SMILES: c1ccc(CCC2NCCc3c2[nH]c2ccccc32)cc1]

or $R_1$ and $R_2$ taken together with X when X is C to form a fused heterocycloalkenyl that is optionally substituted at the heteroatom by alkyl. $R_3$ is selected from Ac, alkyl optionally substituted by: fused cycloakenyl, aryl optionally substituted by alkoxy, $NO_2$, halo; or $R_3$ is selected from one of the following structures:

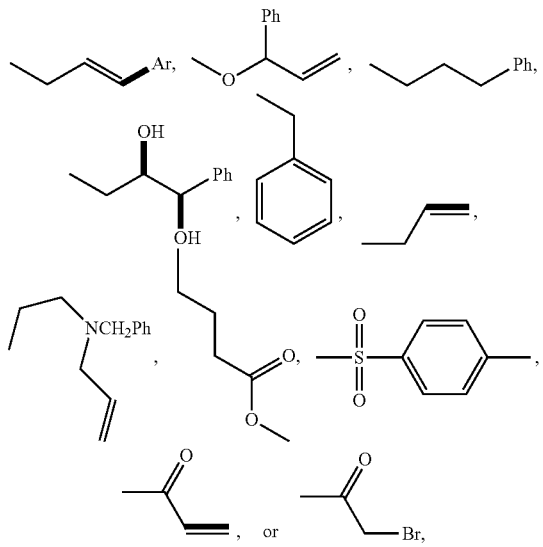

Ar is optionally substituted at any ring position by hydrogen, alkyl, halo, $COOR_4$, $NO_2$, alkoxy, $OOR_4$, and haloalkyl; or $R_3$ together with N form a heterocycloalkyl wherein the ring structure comprises one or more heteroatoms and the one or more heteroatoms is optionally substituted by alkenyl. $R_4$ is alkyl, and $R_5$ is aryl optionally substituted by alkyl.

In certain embodiments, compounds of the invention may be represented by formula (II):

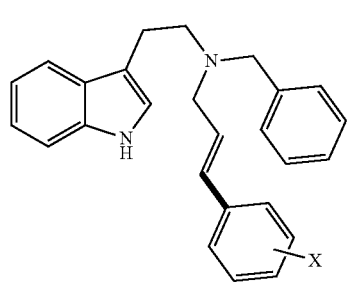

in which X is selected from hydrogen, alkyl, halo, haloalkyl, or $COOR_6$, wherein $R_6$ is alkyl.

In some embodiments, compounds of the invention may be represented by formula (III):

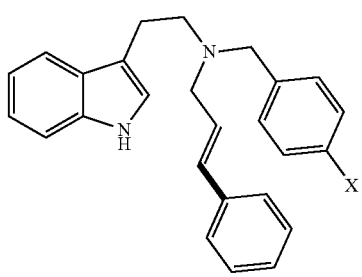
(III)

in which X is selected from alkyl, alkoxy, halo, or NO$_2$.

Certain compounds of the invention may be represented by formula (IV):

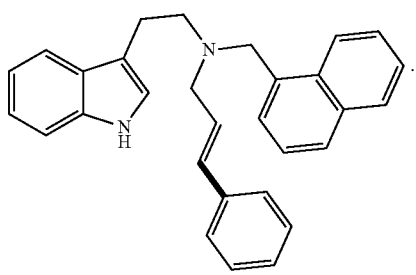
(IV)

In various embodiments, compounds of the invention may be represented by formula (V):

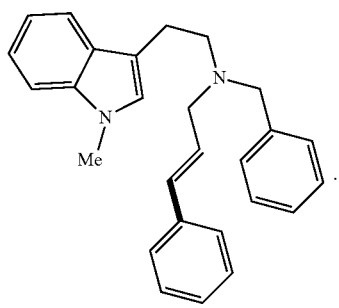
(V)

In certain embodiments, compounds of the invention may be represented by formula (VI):

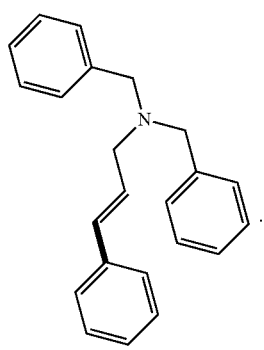
(VI)

Certain compounds of the invention may be represented by formula (VII):

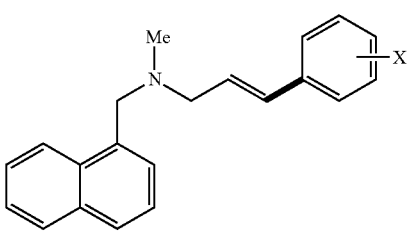
(VII)

in which X is selected from alkyl, halo, alkoxy, NO$_2$, or COOR$_6$, wherein R$_6$ is alkyl.

In certain embodiments, compounds of the invention may be represented by formula (III):

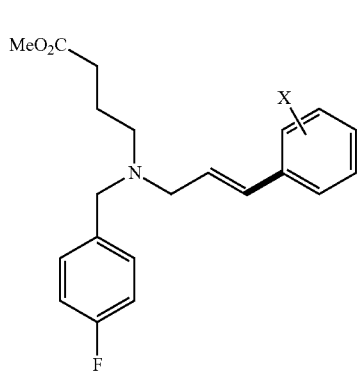
(VIII)

in which X is selected from hydrogen, alkyl, halo, or COOR$_6$, wherein R$_6$ is alkyl.

In some embodiments, compounds of the invention may be represented by formula (IX):

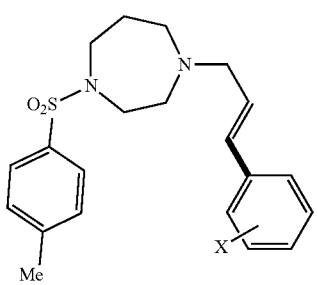
(IX)

in which X is selected from hydrogen, alkyl, or halo.

In certain embodiments, compounds of the invention may be represented by formula (X):

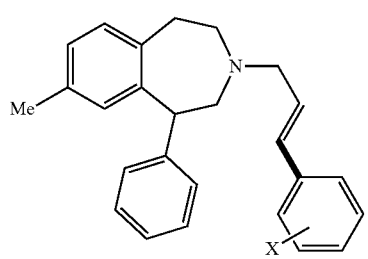
(X)

in which X is selected from hydrogen, alkyl, haloalkyl, or halo.

In various embodiments, compounds of the invention may be represented by formula (XI):

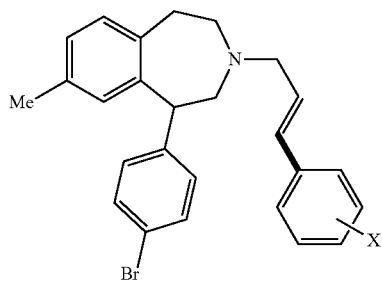

(XI)

in which X is selected from hydrogen, alkyl, or halo.

Certain compounds of the invention may be represented by one of formulas (XII), (XIII), and (XIV):

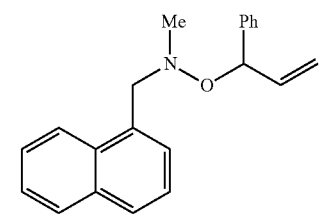

(XII)

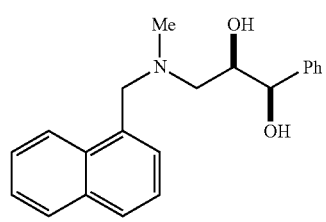

(XIII)

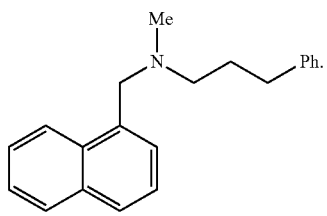

(XIV)

In certain embodiments, compounds of the invention may be represented by formula (XV):

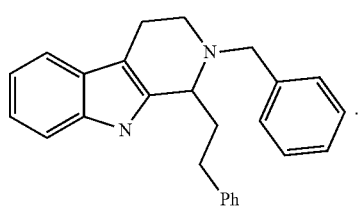

(XV)

In various embodiments, compounds of the invention may be represented by one of the following structures:

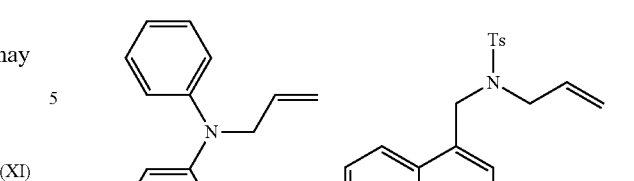

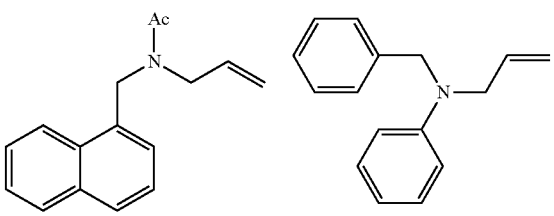

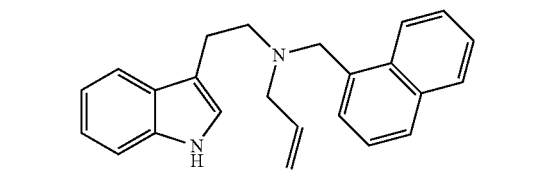

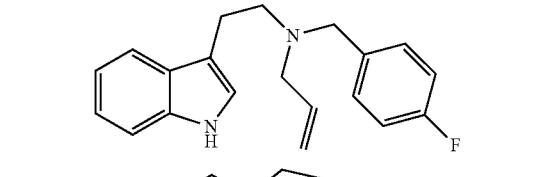

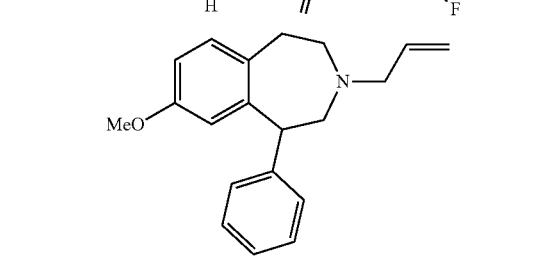

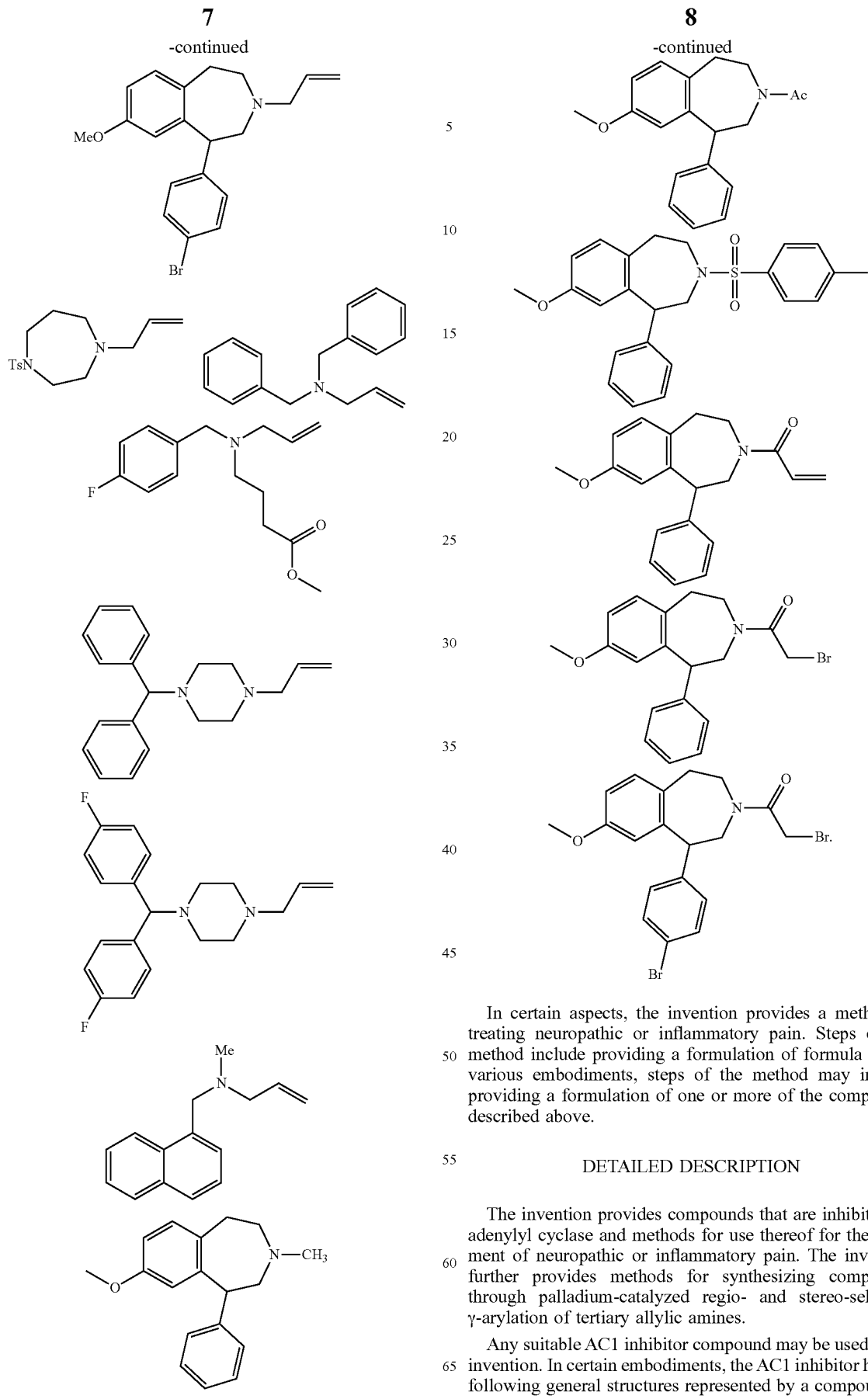

In certain aspects, the invention provides a method of treating neuropathic or inflammatory pain. Steps of the method include providing a formulation of formula (I). In various embodiments, steps of the method may include providing a formulation of one or more of the compounds described above.

DETAILED DESCRIPTION

The invention provides compounds that are inhibitors of adenylyl cyclase and methods for use thereof for the treatment of neuropathic or inflammatory pain. The invention further provides methods for synthesizing compounds through palladium-catalyzed regio- and stereo-selective γ-arylation of tertiary allylic amines.

Any suitable AC1 inhibitor compound may be used in the invention. In certain embodiments, the AC1 inhibitor has the following general structures represented by a compound of formula (I):

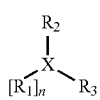
(I)

wherein: X is carbon or nitrogen; n is 0 or 1; $R_1$ is selected from aryl, alkenyl, or alkyl optionally substituted by: aryl optionally substituted by halo, fused cycloalkenyl optionally substituted by halo, or fused heterocycloalkenyl optionally substituted at the heteroatom by alkyl. $R_2$ is selected from Ts, Ac, aryl, or a branched or unbranched alkyl optionally substituted at one or more positions by $COOR_3$, aryl optionally substituted by halo, $NO_2$, alkoxy, fused heterocycloalkenyl optionally substituted by halo, $NO_2$, or alkoxy, or fused heterocycloalkenyl optionally substituted at the heteroatom by alkyl. $R_1$ and $R_2$ may be taken together with X when X is N to form a heterocycloalkyl optionally substituted at the heteroatom by $SO_2R_5$, fused heterocycloalkyl-aryl optionally substituted on the aryl ring by alkyl, Ts, or alkoxy, or $R_1$ and $R_2$ taken together with X when X is N to form the following structure:

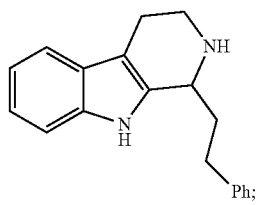 [SMILES: c1ccc(CCC2NCCc3c2[nH]c2ccccc32)cc1]

or $R_1$ and $R_2$ taken together with X when X is C to form a fused heterocycloalkenyl that is optionally substituted at the heteroatom by alkyl. $R_3$ is selected from Ac, alkyl optionally substituted by: fused cycloakenyl, aryl optionally substituted by alkoxy, $NO_2$, halo; or $R_3$ is selected from one of the following structures:

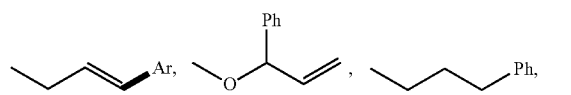

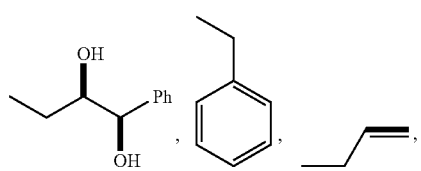

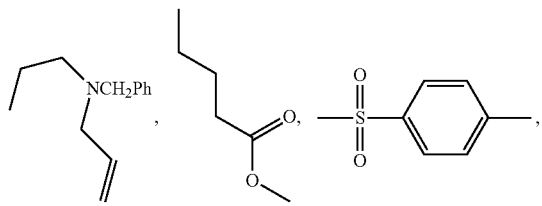

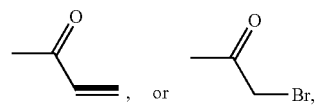

Ar is optionally substituted at any ring position by hydrogen, alkyl, halo, $COOR_4$, $NO_2$, alkoxy, $OOR_4$, and haloalkyl; or $R_3$ together with N form a heterocycloalkyl wherein the ring structure comprises one or more heteroatoms and the one or more heteroatoms is optionally substituted by alkenyl. $R_4$ is alkyl, and $R_5$ is aryl optionally substituted by alkyl.

In certain embodiments, compounds of the invention may have the structures represented by formula (II):

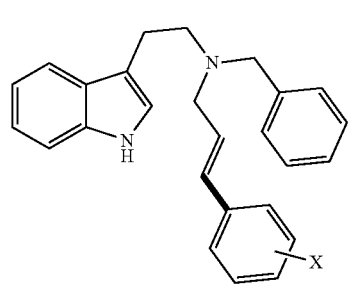
(II)

in which X is selected from hydrogen, alkyl, halo, haloalkyl, or $COOR_6$, wherein $R_6$ is alkyl.

In some embodiments, compounds of the invention may be represented by formula (III):

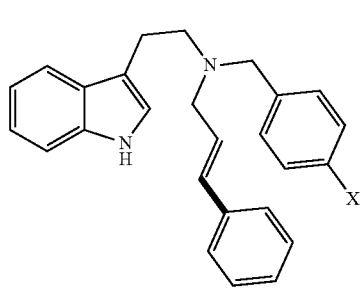
(III)

in which X is selected from alkyl, alkoxy, halo, or $NO_2$.

Certain compounds of the invention may be represented by formula (IV):

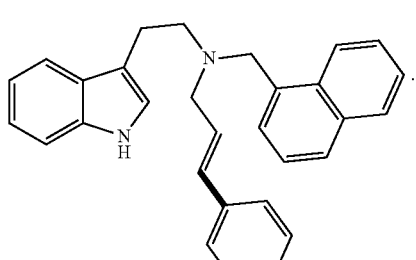
(IV)

In various embodiments, compounds of the invention may be represented by formula (V):

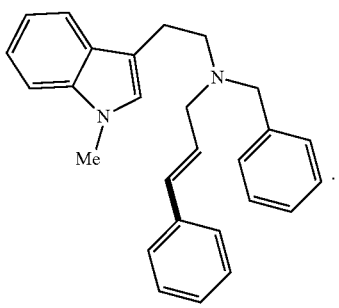

In certain embodiments, compounds of the invention may be represented by formula (VI):

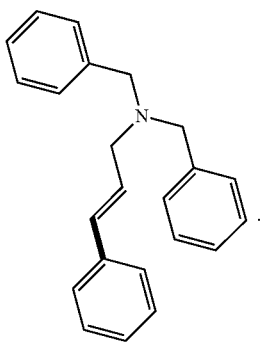

Certain compounds of the invention may be represented by formula (VII):

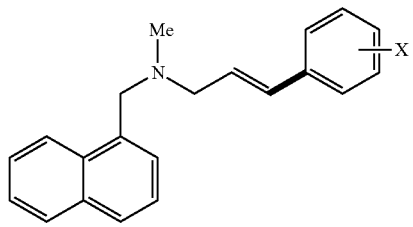

in which X is selected from alkyl, halo, alkoxy, $NO_2$, or $COOR_6$, wherein $R_6$ is alkyl.

In certain embodiments, compounds of the invention may be represented by formula (III):

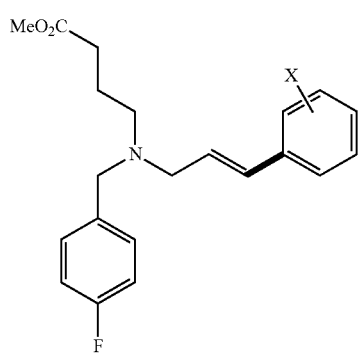

in which X is selected from hydrogen, alkyl, halo, or $COOR_6$, wherein $R_6$ is alkyl.

In some embodiments, compounds of the invention may be represented by formula (IX):

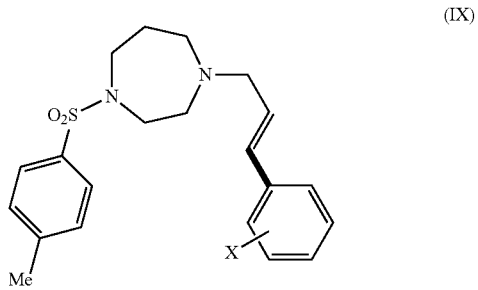

in which X is selected from hydrogen, alkyl, or halo.

In certain embodiments, compounds of the invention may be represented by formula (X):

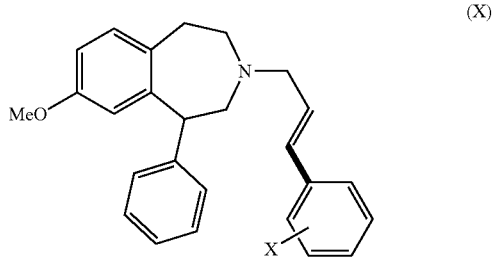

in which X is selected from hydrogen, alkyl, haloalkyl, or halo.

In various embodiments, compounds of the invention may be represented by formula (XI):

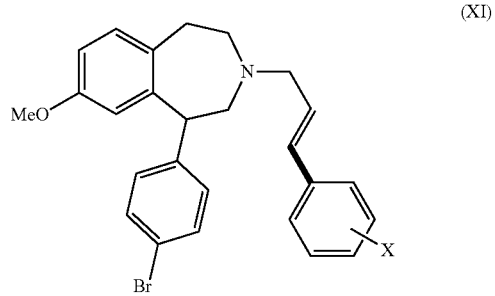

in which X is selected from hydrogen, alkyl, or halo.

Certain compounds of the invention may be represented by one of formulas (XII), (XIII), and (XIV):

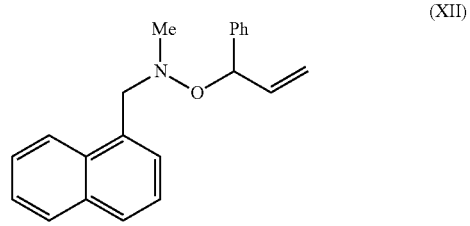

(XIII)
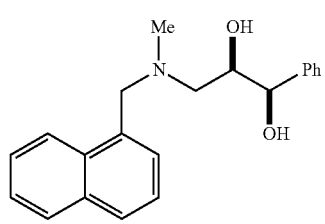
(XIV)
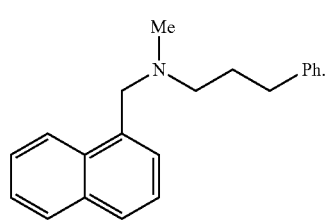
In certain embodiments, compounds of the invention may be represented by formula (XV):
(XV)
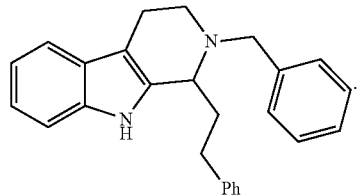
In various embodiments, compounds of the invention may be represented by one of the following structures:
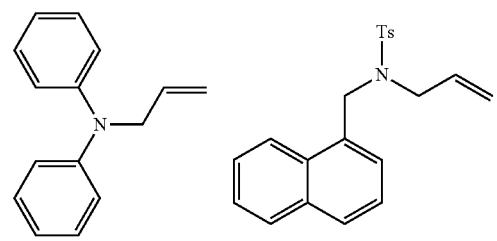
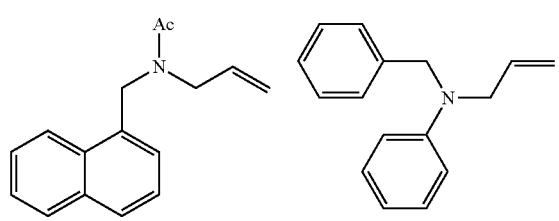
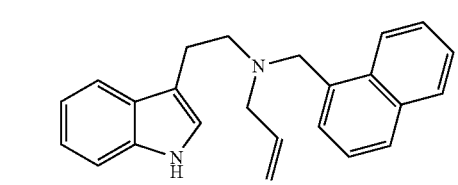
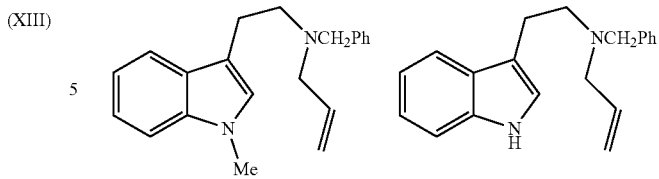
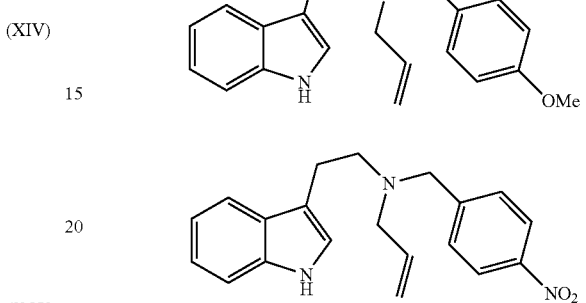
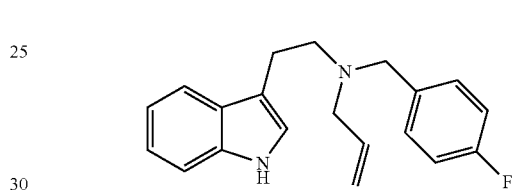
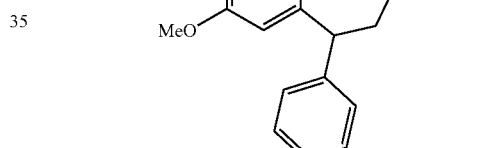
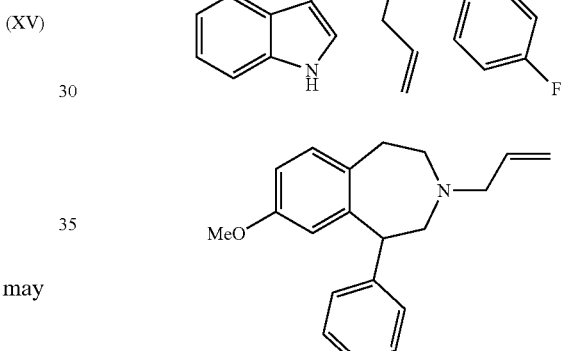
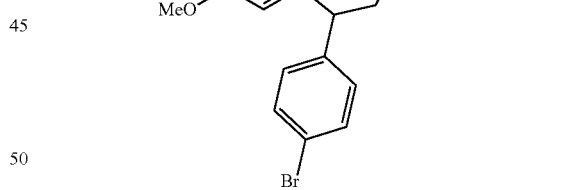
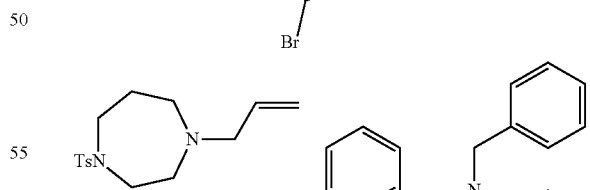
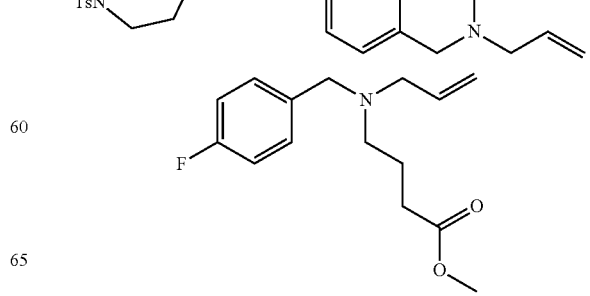

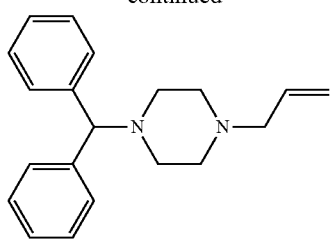

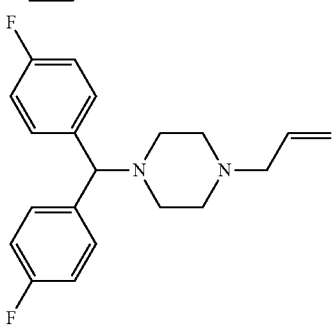

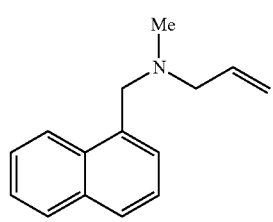

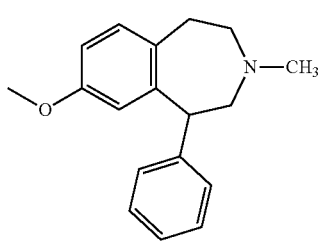

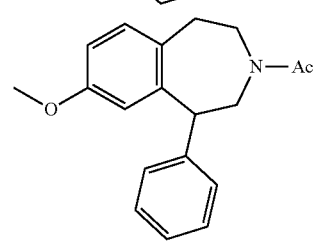

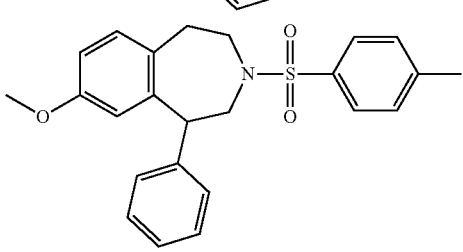

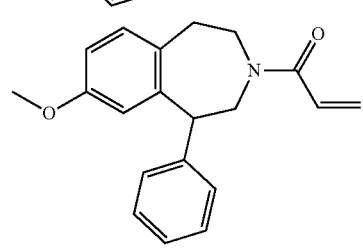

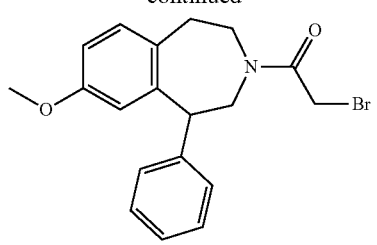

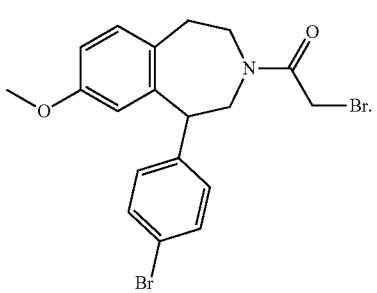

Aryl (Ar) refers to any functional group or substituent derived from an aromatic ring, usually an aromatic hydrocarbon. Exemplary aryl groups are phenyl (Ph), naphthyl, thienyl, or indolyl. An exemplary aryl ring is shown as

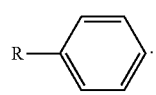

As used herein, one or more of the carbon ring atoms may be substituted by one or more substituents.

Alkyl refers to an alkane missing one hydrogen. Exemplary alkyls include Methyl Ethyl Propyl Butyl Pentyl Hexyl Heptyl Octyl Nonyl Decyl Undecyl Dodecyl. As used herein, the alkyl may be a straight chain alkyl or a branched chain alkyl. As used herein, one or more of the carbon atoms may be substituted by one or more substituents.

A cycloalkyl refers to a ring structure composed of single bonded carbon atoms. The ring structure can have anywhere from 3 to 20 atoms, such as 3, 4, 5, 6, 7, 8, 9, 10, etc. Exemplary cycloalkyl structures are

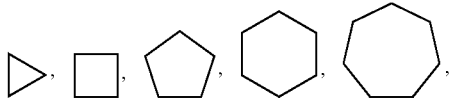

As used herein, one or more of the carbon ring atoms may be substituted by one or more substituents.

A heterocycloalkyl refers a cycloalkyl in which one of the ring carbons is substituted by a heteroatom. An exemplary heterocycloalkyl is

As used herein, one or more carbon ring atoms may be substituted by one or more substituents and/or the heteroatom may be substituted by one or more substituents.

Alkenyl refers to an alkyl group having one or more double bonds. Any of the above mentioned alkyl groups can also be transformed into alkenyl groups. An exemplary structure of an alkenyl group is

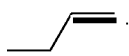

As used herein, the alkenyl may be a straight chain alkenyl or a branched chain alkenyl. As used herein, one or more carbon atoms of the alkenyl group may be substituted by one or more substituents.

A fused cycloalkenyl refers to a fused ring structure having one or more double bonds. The fused structure can include two or more rings. Exemplary fused ring structures have between 6 and 20 carbon atoms, for example 8, 10, 12, 14, 16, or 18 carbon atoms. An exemplary structure of a fused cycloakenyl is

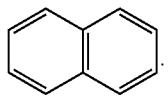

As used herein, one or more carbon ring atoms may be substituted by one or more substituents.

A fused heterocycloalkenyl is a fused cycloalkenyl as described above in which one or more of the carbon ring atoms is substituted by a heteroatom. An exemplary structure of a fused heterocycloalkenyl is

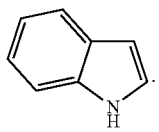

As used herein, one or more carbon ring atoms may be substituted by one or more substituents and/or the heteroatom may be substituted by one or more substituents.

A heteroatom refers to any atom that is not carbon or hydrogen. Usually, the heteroatom indicates a non-carbon atom having replaced a carbon in the backbone of the molecular structure, e.g., of an alkyl, alkenyl, heteroalkyl, aryl, fused cycloalkyl, fused cycloalkenyl. Exemplary heteroatoms are nitrogen and sulfur.

Halo refers to any halogen bonded to a carbon. Exemplary halo groups are iodine, chlorine, bromine, or fluorine.

Ts refers to tosyl ($CH_3C_6H_4SO_2$).

Ac refers to acetyl ($CH_3C=O$).

Alkoxy refers to an alkyl group singular bonded to oxygen (R—O). Exemplary Alkoxy groups include methoxy (O-Me) and ethoxy (O-Et).

A fused heterocycloalkyl-aryl refers to a heterocycloalkyl group fused to an aryl group. An exemplary fused heterocycloalkyl-aryl is

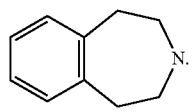

As used herein, one or more carbon ring atoms may be substituted by one or more substituents and/or the heteroatom may be substituted by one or more substituents.

In certain aspects, the invention provides a method of treating neuropathic or inflammatory pain. Steps of the method include providing compounds of the invention as an adenylyl cyclase inhibitor. Compounds of the invention may be AC1 inhibitors. The compounds may have an $IC_{50}$ in the μM range and more preferably in the nM or pM range. The compounds of the present invention may have an $IC_{50}$ value for inhibition of AC1 from about 1 μM to about 50 μM or more preferably, from about 1 μM to about 20 μM. Compounds of the invention may have an $IC_{50}$ value for inhibition of AC1 from about 1 nM to about 1 μM. Table 1 shows the $IC_{50}$ values for inhibition of the A23187-mediated cAMP response of AC1. HEK cells stably expressing AC1 were treated with inhibitors for 30 min, and subsequently incubated with 3 μM A23187 in the presence of 2 mM IBMX. Data represent the average and S.E.M. of at least three independent experiments.

TABLE 1

| Compound | $IC_{50}$ (μM) |
| --- | --- |
| II, X = p-I | 10.23 (±1.20) |
| II, X = p-F | 12.89 (±3.45) |
| II, X = p-BR | 6.91 (±0.50) |
| IV | 8.95 (±1.55) |
| X, X = H | 16.93 (±7.59) |
| X, X = p-Me | 16.66 (±4.91) |
| X, X = p-F | 14.75 (±1.31) |
| X, X = p-Cl | 9.10 (±0.82) |
| II, X = H | 9.92 (±2.28) |

The invention generally provides pharmaceutically effective compositions of AC1 inhibitor compounds, as well as methods of use that include administering compounds or compositions of the invention for the treatment of a patient. Suitable routes of administration include oral, buccal, topical (including trans-dermal), etc. In one embodiment of the present invention there are provided methods of treating a patient have neuroinflammatory and/or neuropathic pain with the compounds of the present invention. Notably, AC1 has been associated with chronic pain responses in several regions of the central nervous system. Inhibition of AC1 by the compounds of the present invention may result in analgesic effects in both neuroinflammatory and neuropathic pain in a patient. The patient may be any mammal in need of treatment of neuroinflammatory and/or neuropathic pain including, but not limited to, humans, dogs cats, horses or livestock.

The effective dosage of each agent can readily be determined by the skilled person, having regard to typical factors each as the age, weight, sex and clinical history of the patient. Preferably, the dose of compounds of the present invention will be administered at doses from about 0.1 mg to about 250 mg of body weight. In some embodiments, the dose of compounds of the present invention will be from about 1 mg to about 60 mg.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

When the compounds of the present invention, for example a compound of formula (I) are administered as pharmaceuticals, to humans and mammals, they can be given per se or as a pharmaceutical composition containing, for example, 0.1 to 99.5% (more preferably, 0.5 to 90%) of active ingredient, i.e., at least one a compound of formula (I) and/or derivative thereof, in combination with a pharmaceutically acceptable carrier.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects; will range from about 0.1 mg to about 250 mg per kilogram of body weight per day, more preferably from about 1 mg to about 60 mg per kg per day.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the compounds of the present invention, or functional derivatives thereof. An "effective amount" is the amount as defined herein in the definition section and refers to an amount effective, at dosages and for periods of time necessary, to achieve the desired therapeutic result, e.g., a diminishment or prevention of effects associated with neuropathic and/or inflammatory pain. A therapeutically effective amount of a compound of the present invention or functional derivatives thereof may vary according to factors such as the disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to, or at an earlier stage of disease, the prophylactically effective amount may be less than the therapeutically effective amount. A prophylactically or therapeutically effective amount is also one in which any toxic or detrimental effects of the compound are outweighed by the beneficial effects.

The term "synergy" or "synergistic" as used herein, refers to the interaction of two or more agents so that their combined effect is greater than each of their individual effects at the same dose alone.

Dosage regimens may be adjusted to provide the optimum desired response (e.g. a therapeutic or prophylactic response). For example, a single bolus may be administered, several divided doses may be administered over time or the dose may be proportionally reduced or increased as indicated by the exigency of the therapeutic situation. It is especially advantageous to formulate parenteral compositions in dosage unit form for ease of administration and uniformity of dosage. Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the patient.

The term "dosage unit" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound, and (b) the limitations inherent in the art of compounding such an active compound for the treatment of sensitivity in individuals.

In some embodiments, therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is sufficient to reduce or inhibit neuropathic and/or inflammatory pain in a subject. In some embodiments, the therapeutically effective amount is sufficient to eliminate neuropathic and/or inflammatory pain in a subject.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the compounds of the invention or functional derivatives thereof, and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more compounds of the invention or functional derivatives thereof are optionally tested in one or more appropriate in vitro and/or in vivo animal models of disease, such as models of neuropathic and/or inflammatory pain, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of compounds of the invention or functional derivatives thereof at various concentrations, e.g., as applied to the mass and overall health of the patient. Administration can be accomplished via single or divided doses.

Administering typically involves administering pharmaceutically acceptable dosage forms, which means dosage forms of compounds described herein, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety. Administering may be carried out orally, intradermally, intramuscularly, intraperitoneally, intravenously, subcutaneously, or intranasally. Compounds may be administered alone or with suitable pharmaceutical carriers, and can be in solid or liquid form, such as tablets, capsules, powders, solutions, suspensions, or emulsions.

A pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. No. 4,256,108, U.S. Pat. No. 4,166,452 and U.S. Pat. No. 4,265,874, to form osmotic therapeutic tablets for control release.

Formulations for oral use may also be presented as hard gelatin capsules in which the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Formulations may also include complexes of the parent (unionized) compounds with derivatives of β-cyclodextrin, especially hydroxypropyl-β-cyclodextrin.

An alternative oral formulation can be achieved using a controlled-release formulation, where the compound is encapsulated in an enteric coating.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Each active agent may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions are suitable. Topical application includes the use of mouth washes and gargles.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin. Examples of suitable carriers, diluents, solvents, or vehicles include water, ethanol, polyols, suitable mixtures thereof, vegetable oils (such as olive oil), and injectable organic esters such as ethyl oleate.

Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response, and the like, and are commensurate with a reasonable benefit/risk ratio.

The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: "Design of Prodrugs," H. Bundgaard, ed., Elsevier (1985); "Methods in Enzymology," K. Widder et al, Ed., Academic Press, 42, p. 309-396 (1985); "A Textbook of Drug Design and Development," Krogsgaard-Larsen and H. Bundgaard, ed., Chapter 5; "Design and Applications of Prodrugs," p. 113-191 (1991); "Advanced Drug Delivery Reviews," H. Bundgard, 8, p. 1-38 (1992); Journal of Pharmaceutical Sciences 77:285 (1988); Nakeya et al, Chem. Pharm. Bull. 32:692 (1984); Higuchi et al., "Prodrugs as Novel Delivery Systems," Vol. 14 of the A.C.S. Symposium Series, and Bioreversible Carriers in Drug Design, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

The present invention further relates to methods of synthesizing γ-arylated N,N-dialkylallylamines. In certain embodiments, methods of the invention relate to synthesizing compounds of the invention discussed above. Synthesis methods may comprise a mild palladium-catalyzed regio- and stereo-selective γ-arylation of N,N-dialkylallylamines. Compounds may be assessed for therapeutic potential for treating neuropathic and inflammatory pain through adenylyl cyclase inhibition.

Various strategies have been developed for the construction of γ-arylated N,Ndialkylallylamine derivatives. One of the most desirable and straightforward ways would be a Heck arylation of N,N-dialkylallylamines at the terminal olefinic carbon (γ-position). In general, Heck arylations work well with activated and biased olefins such as acrylates and styrenes. See, Beletskaya, et al., The heck reaction as a sharpening stone of palladium catalysis, Chem. Rev. 2000 Aug. 9; 100(8):3009-66, incorporated herein by reference. Recently, significant progresses in the Heck arylation of electronically nonbiased olefins have been made. See, M. Oestreich, Breaking News on the Enantioselective Intermolecular Heck Reaction (Highlight), Angew. Chem. 2014, 126, 2314-2317; M. Oestreich, Breaking News on the Enantioselective Intermolecular Heck Reaction (Highlight), Angew. Chem. 2014, 126, 2314-2317; Olofsson, et al., Highly Regioselective Palladium-Catalyzed Internal Arylation of Allyltrimethylsilane with Aryl Triflates, J. Org. Chem. 1998, 63, 5076-5079; Werner, et al., Enantioselective Heck Arylations of Acyclic Alkenyl Alcohols Using a Redox-Relay Strategy, Science 2012, 338, 1455-1458; Werner, et al., Operationally Simple and Highly (E)-Styrenyl-Selective Heck Reactions of Electronically Nonbiased Olefins, J. Am. Chem. Soc. 2011, 133, 9692-9695; Werner, et al., A Highly Selective and General Palladium Catalyst for the Oxidative Heck Reaction of Electronically Nonbiased Olefins, J. Am. Chem. Soc. 2010, 132, 13981-13983; Hu, et al., Palladium-Catalyzed Asymmetric Intermolecular Cyclization, Angew. Chem. 2013, 125, 8838-8842; Wu, et al., Asymmetric Intermolecular Heck Reaction of Aryl Halides, J. Am. Chem. Soc. 2014, 136, 650-652; Qin, et al., Intermolecular Mizoroki-Heck Reaction of Aliphatic Olefins with High Selectivity for Substitution at the Internal Position, Angew. Chem. 2012, 124, 6017-6021; Zheng, et al., Catalyst-Controlled Regioselectivity in the Synthesis of Branched Conjugated Dienes via Aerobic Oxidative Heck Reactions, J. Am. Chem. Soc. 2012, 134, 16496-16499; Tasker, et al., Nickel-Catalyzed Mizoroki-Heck Reaction of Aryl Sulfonates and Chlorides with Electronically Unbiased Terminal Olefins: High Selectivity for Branched Products, Angew. Chem. 2014, 126, 1889-1892; each incorporated by reference herein. Because of this, regio- and stereo-selective arylation of simple terminal olefins such as allylic alcohols, homoallylic alcohols and other un-activated olefins have become important and powerful synthetic tools in making complex and functional molecules.

Despite these significant advancements, stereoselective γ-arylation of N,Ndialkylallylamines persist as a great synthetic challenge due to the following difficulties presented by N,N-dialkylallylamine substrates. One difficulty is the strong basicity and coordinating capability of these tertiary amines make most of the Heck arylation conditions invalid for •-arylation. For example, groups have reported palladium-catalyzed Heck arylation of N,N-dialkylallylamines and in both cases, β-arylated products were obtained predominantly due to the intrinsic directing ability of the nitrogen atom. See Olofsson, et al., Highly Regioselective Palladium-Catalyzed β-Arylation of N,N-Dialkylallylamines, J. Org. Chem. 2000, 65, 7235-7239; Wu, et al., β-Regioselective intermolecular Heck arylation of N,N-disubstituted allylamines, Tetrahedron Lett. 2001, 42, 159-162; each incorporated herein by reference.

Another challenge presented by N,N-dialkylallylamine substrates is that the oxidative addition of palladium (0) catalyst with allylamines to form π-allyl palladium species competes with the Heck arylation, which renders allylamines as allyl group donors or an amine source. Examples of using allylamines as allyl donors have been reported. see, Zhao, et al., C—N Bond Cleavage of Allylic Amines via Hydrogen Bond Activation with Alcohol Solvents in Pd-Catalyzed Allylic Alkylation of Carbonyl Compounds, J. Am. Chem. Soc. 2011, 133, 19354-19357; Li, et al., Regioselective and Stereospecific Cross-Coupling of Primary Allylic Amines with Boronic Acids and Boronates through Palladium-Catalyzed C[BOND]N Bond Cleavage, Angew. Chem. 2012, 124, 3022-3025; Wu, et al., Direct Substitution of Primary Allylic Amines with Sulfinate Salts, J. Am. Chem. Soc. 2012, 134, 14694-14697; each of which is incorporated herein by reference.

Selective β-hydride elimination (Ha vs Hb) to form the desired product remains as an issue with N,N-dialkylallylamine substrates as well. In order to get around these intrinsic competing factors and obtain desired γ-arylated products, methods of the prior art employs protecting and directing group strategies. See, Prediger, et al., Substrate-Directable Heck Reactions with Arenediazonium Salts. The Regio- and Stereoselective Arylation of Allylamine Derivatives and Applications in the Synthesis of Naftifine and Abamines, J. Org. Chem. 2011, 76, 7737-7749; Ripin, et al., Evaluation of Kilogram-Scale Sonagashira, Suzuki, and Heck Coupling Routes to Oncology Candidate CP-724,714; Alvisi, et al., Regio- and Stereochemical Aspects of the Palladium-Catalyzed Desilylation-Arylation of Substituted Vinylsilanes, J. Org. Chem. 1996, 61, 7139-7146; Dong, et al., Indoles from o-Haloanilines: Syntheses of Tryptamines and Tryptophols via Regioselective Hydroformylation of Functionalized Anilines, J. Org. Chem. 1997, 62, 6464-6465; Reddington, et al., Convenient synthesis of (E)-5-aminoallyl-2'-deoxycytidine and some related derivatives, Tetrahedron Lett. 2011, 52, 181-183; Cacchi, et al., Heck reaction of arenediazonium salts with N,N-diprotected allylamines. Synthesis of cinnamylamines and indoles, Org. Biomol. Chem. 2011, 9, 1727-1730; Millet, et al., Palladium-Catalyzed γ-Selective Arylation of Zincated Boc-Allylamines, Org. Lett. 2014, 16, 3998-4000; each incorporated by reference herein. In such methods, the basic nitrogen atoms are masked as amides, carbamates, etc. and the protecting groups also serve as directing groups to ensure the arylation takes place at the γ-position. These methods can result in poor regioselectivity or β-arylation. In addition to the installation of the required protecting and directing groups in the known methods, extra steps are required to remove them or convert them to the desired alkyl groups.

In contrast to the prior art, the methods of the present invention provide a straightforward stereoselective synthesis of γarylation of N,N-dialkylallylamines without the need for protection and/or directing groups. The synthetic methods of the present invention are based on a modification of the Heck arylation. The equation given below is an example of the methods of the present invention:

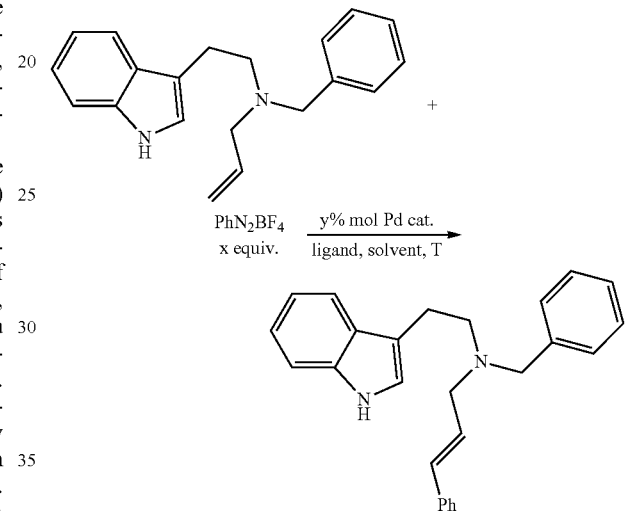

In one embodiment of the present invention, the ligand may be, but not limited to, a 2,2'-bipyridine ligand. While not wishing to be bound by theory, it is thought that the 2,2'-bipyridine ligand overrides the intrinsic coordination of the tertiary nitrogen with the palladium center to control the regioselectivity of the above reaction. In another embodiment of the present invention, the solvent for the synthetic method may be, but not limited to, THF, $CH_3CN$, DMSO, DMA, DMF or combinations thereof. In a preferred embodiment, the solvent is DMF. In certain embodiments of the present invention, the synthesis of the present invention can be carried out at or near room temperature.

In some embodiments, the palladium catalyst may be, but not limited to, $Pd(dba)_2$, $Pd(OAc)_2$, $PdCl_2$, $Pd(PPh_3)_4$. In a preferred embodiment the palladium catalyst is $Pd(dba)_2$.

The synthetic method of the present invention is very general and compatible with many functional groups including halogens (I, Br, Cl and F), ester groups, amides, nitro group, and indoles. Diazonium salts with both electron withdrawing and electron donating groups are effective coupling partners. A variety of γ-arylated N,N-dialkylallylamines may be produced in good to excellent yield using methods of the invention, including those derived from azepanes, diazepanes, and piperazines.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

The invention now being generally described, it will be more readily understood by reference to the following examples, which are included merely for purposes of illustration of certain aspects and embodiments of the present invention, and are not intended to limit the invention.

Example 1

A mixture of palladium catalyst and ligand in DMF or DMA was stirred at room temperature for 20 minutes under argon before the reactants were added using the following equation:

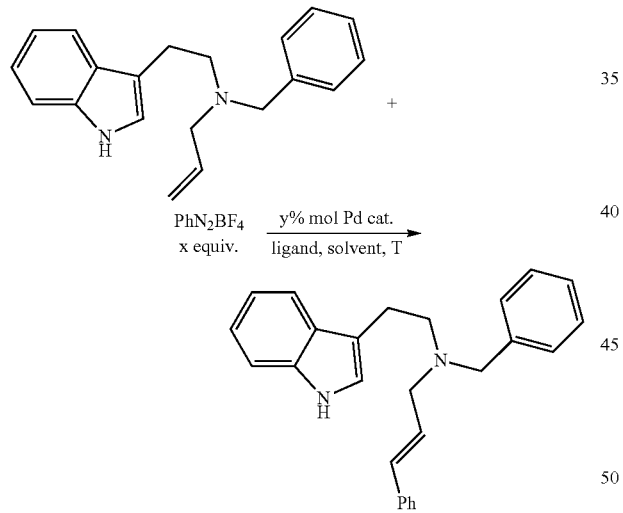

Isolated reaction yield is shown for several reactions in table 2.

TABLE 2

| entry | Pd cat. | x | y | solvent | ligand | base | yield (%)[b] |
|---|---|---|---|---|---|---|---|
| 1 | Pd(dba)$_2$ | 1.5 | 5 | DMF | L1 | — | 54 |
| 2 | Pd(dba)$_2$ | 1.5 | 5 | DMA | L1 | — | 33 |
| 3 | Pd(dba)$_2$ | 1.5 | 5 | DMF | L1 | — | 49[c] |
| 4 | Pd(dba)$_2$ | 1.5 | 5 | DMF | L1 | Et$_3$N | — |
| 5 | Pd(dba)$_2$ | 1.5 | 5 | DMF | L1 | K$_2$CO$_3$ | — |
| 6 | Pd(dba)$_2$ | 2.0 | 5 | DMF | L1 | — | 73 |
| 7 | Pd(dba)$_2$ | 2.5 | 5 | DMF | L1 | — | 71 |
| 8 | Pd(dba)$_2$ | 2.0 | 8 | DMF | L1 | — | 80 |
| 9 | Pd(dba)$_2$ | 2.0 | 10 | DMF | L1 | — | 85 |

TABLE 2-continued

| entry | Pd cat. | x | y | solvent | ligand | base | yield (%)[b] |
|---|---|---|---|---|---|---|---|
| 10 | Pd(dba)$_2$ | 2.0 | 10 | DMF | L2 | — | 81 |
| 11 | Pd(dba)$_2$ | 2.0 | 10 | DMF | L3 | — | 54 |
| 12 | Pd(dba)$_2$ | 2.0 | 10 | DMF | L4 | — | 90 |
| 13 | Pd(dba)$_2$ | 2.0 | 10 | DMF | — | — | 54 |
| 14 | Pd(OAc)$_2$ | 2.0 | 10 | DMF | L4 | — | 55 |
| 15 | PdCl$_2$ | 2.0 | 10 | DMF | L4 | — | trace |
| 16 | Pd(PPh$_3$)$_4$ | 2.0 | 10 | DMF | L4 | — | trace |

[c] at 60° C.

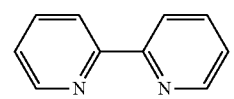

L1

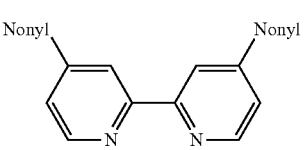

L2

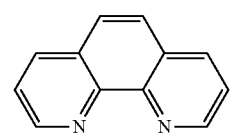

L3

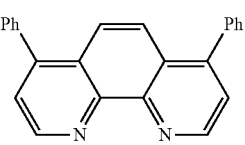

L4

Since aryl diazonium salts have been used frequently in Heck arylation of non-activated olefins, investigation started with phenyl diazonium tetrafluoroborate and a relatively complex and challenging allylic amine substrate:

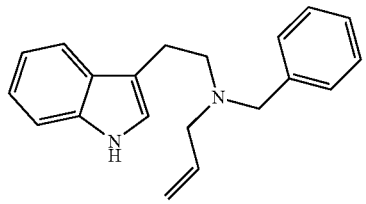

(5a)

In order to override the intrinsic coordination of the tertiary nitrogen with palladium center to control the regioselectivity, 2,2'-bipyridine ligand L1 was selected. When 5a, at 1 equiv., and PhN$_2$BF$_4$ (6a), at 1.5 equiv., were subjected to the conditions of Pd(dba)$_2$ with L1 (Pd:L=1:1) at room temperature in DMF, desired product:

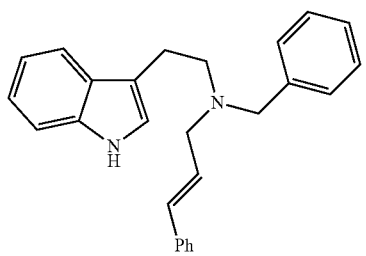 [SMILES: C(=C\c1ccccc1)/CN(CCc1c[nH]c2ccccc12)Cc1ccccc1]

was obtained in 54% yield. Other solvents such as THF, CH$_3$CN, DMSO, and DMA were found inferior to DMF or found to completely inhibit the reaction. Slightly reduced yield was obtained when the reaction was conducted at an elevated temperature (entry 3 in table 2). Bases such as triethylamine and K$_2$CO$_3$ shut down the reaction (entries 4-5 in table 2). Further increase in the amount of 6a or the catalyst-ligand loading was found to be of beneficial effect. Among the four nitrogen-containing bidentate ligands tested, L4 gave the best result (entry 12 in table 2). The reaction yield dropped significantly when several bidentate phosphine ligands were used (see the supporting information). Other palladium catalysts including PdCl$_2$, Pd(PPh$_3$)$_4$ and Pd(OAc)$_2$ were less effective than Pd(dba)2. Overall, under the optimized condition (entry 12 in table 2), desired product could be produced in 90% yield with excellent regio- and stereo-selectivity.

Example 2

Substrate scope was evaluated using the reaction above. The reaction is very general and compatible with many functional groups including halogens (I, Br, Cl and F), ester groups, amides, nitro group, and indoles. Diazonium salts with both electron withdrawing and electron donating groups are effective coupling partners. A variety of γ-arylated N,Ndialkylallylamines were produced in good to excellent yield, including those derived from azepanes, diazepanes, and piperazines. Notably, the reaction was used to produce naftifine in 90% yield. When reaction was conducted at gram scale, naftifine was obtained at 72% yield. Cinnarizine and flunarizine were synthesized as well.

Additionally, these γ-arylated products were converted to other useful products. For example, amine oxidation followed by [2,3]-sigmatropic rearrangement converted naftifine to the following compound:

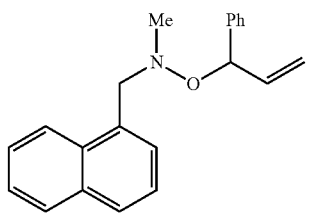 [SMILES: C=CC(ON(C)Cc1cccc2ccccc12)c1ccccc1]

Under argon atmosphere, to a mixture of naftifine (57.4 mg, 0.2 mmol) and Na$_2$CO$_3$ in the DCM was added m-CPBA (111 mg, 0.5 mmol) at −78° C. The reaction mixture was stirred for 1 h before it was quenched by aqueous NH$_4$Cl. The organic layer was separated and the aqueous layer was extracted with EtOAc three times. The combined organic extracts were washed by aqueous NaHCO$_3$ (three times) then aqueous NaCl (three times). The organic layer was dried over Na$_2$SO$_4$ and concentrated in vacuo to afford the crude product. The crude product was dissolved in 3 mL acetone and the mixture was stirred for 5 h at room temperature before the solvent was removed. The residue was purified by column chromatography with a mixture of Hexane and EtOAc as eluent to afford the above product at a 60% yield.

Dihydroxylation converted naftifine to the following compound:

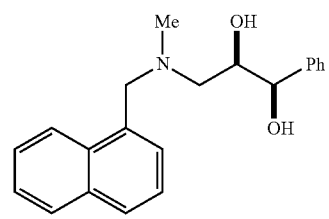 [SMILES: CN(Cc1cccc2ccccc12)C[C@@H](O)[C@H](O)c1ccccc1]

Under argon atmosphere, to a mixture of naftifine (28.7 mg, 0.1 mmol) and NMO (17.6 mg, 0.15 mmol) in acetone/H$_2$O (2 mL, 1:1) was added OsO$_4$ (0.06 mL, 4% in water). The reaction mixture was stirred at room temperature for 24 h before it was quenched with aqueous Na$_2$S$_2$O$_3$. The organic layer was separated and the aqueous layer was extracted with EtOAc three times. The combined organic extracts were dried over Na$_2$SO$_4$ and concentrated in vacuo. The residue was purified by column chromatography with a mixture of Hexane and EtOAc as eluent to afford the above product at 78% yield.

Hydrogenation converted naftifine to the following compound:

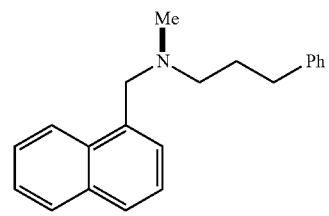

A mixture of naftifine (57.4 mg, 0.2 mmol) and RhCl(PPh$_3$)$_3$ (9.2 mg, 0.01 mmol) in toluene under H$_2$ (balloon) was stirred at 70° C. for 24 h. Then the reaction was quenched with aqueous NH$_4$Cl. The organic layer was separated and the aqueous layer was extracted with EtOAc three times. The combined organic extracts were dried over Na$_2$SO$_4$ and concentrated in vacuo. The residue was purified by column chromatography (the silica gel was treated with Et$_3$N) with a mixture of Hexane and EtOAc as eluent to afford the above product (83% yield).

A one-pot double bond isomerization followed by Picktet-Spengler reaction converted

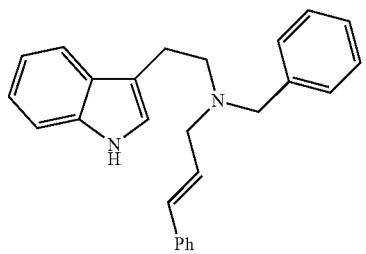 [SMILES: C(=C\c1ccccc1)/CN(CCc1c[nH]c2ccccc12)Cc1ccccc1]

to tetrahydro-β-carboline:

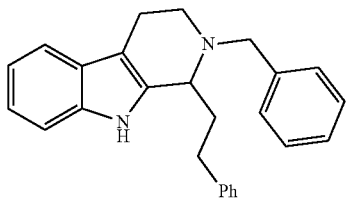 [SMILES: c1ccc(CCC2c3[nH]c4ccccc4c3CCN2Cc2ccccc2)cc1]

The latter product representing the core structure of many bioactive natural products and pharmaceutical molecules. Under argon atmosphere, a mixture of the compound represented by Formula (II), X=H (29 mg, 0.1 mmol) and RhCl(PPh$_3$)$_3$ (4.5 mg, 0.005 mmol) in toluene was stirred at 110° C. for 13 h. The reaction was quenched with aqueous NH$_4$Cl. The organic layer was separated and the aqueous layer was extracted with EtOAc three times. The combined organic extracts were dried over Na$_2$SO$_4$ and concentrated in vacuo. The residue was purified by column chromatography (the silica gel was treated with Et$_3$N) with a mixture of Hexane and EtOAc as eluent to afford the compound above at 73% yield.

Example 3

N-(2-(1H-indol-3-yl)ethyl)-N-(4-fluorobenzyl)prop-2-en-1-amine (5b)

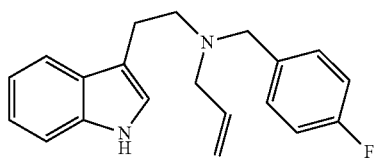 [SMILES: C=CCN(CCc1c[nH]c2ccccc12)Cc1ccc(F)cc1]

79% yield; H NMR (400 MHz, CDCl$_3$) δ 7.93 (br s, 1H), 7.53 (d, J=7.4 Hz, 1H), 7.35-6.96 (m, 8H), 6.01-5.91 (m, 1H), 5.28-5.19 (m, 2H), 3.68 (s, 2H), 3.24 (d, J=5.9 Hz, 2H), 2.99-2.95 (m, 2H), 2.85-2.81 (m, 2H); C NMR (100 MHz, CDCl$_3$) δ 161.8 (d, $J_{C-F}$=244.2 Hz), 136.1, 135.8, 135.3, 130.2 (d, $J_{C-F}$=7.6 Hz), 127.5, 121.9, 121.4, 119.1, 118.8, 117.3, 114.9 (d, $J_{C-F}$=21.2 Hz), 114.5, 111.0, 57.3, 56.7, 53.9, 23.0; F NMR (376 MHz, CDCl$_3$) δ −117.84; IR (neat): ν=3415, 1507, 1456, 1220, 1090 cm$^{-1}$; MS (ESI): m/z 307.3 [M−H]$^-$.

Example 4

N-benzyl-N-(2-(1-methyl-1H-indol-3-yl)ethyl)prop-2-en-1-amine (5d)

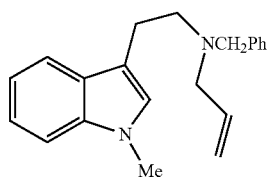

80% yield; H NMR (400 MHz, CDCl$_3$) δ 7.60 (d, J=7.8 Hz, 1H), 7.48-7.28 (m, 7H), 7.17 (t, J=6.9 Hz, 1H), 6.88 (s, 1H), 6.11-6.00 (m, 1H), 5.33-5.26 (m, 2H), 3.80 (s, 2H), 3.76 (s, 3H), 3.32 (d, J=6.1 Hz, 2H), 3.07-3.03 (m, 2H), 2.93-2.89 (m, 2H); C NMR (100 MHz, CDCl$_3$) δ 139.7, 136.9, 136.1, 129.0, 128.2, 128.0, 126.8, 126.3, 121.4, 119.0, 118.6, 117.3, 113.1, 109.1, 58.2, 57.0, 54.3, 32.5, 22.9; IR (neat): ν=1483, 1472, 1374, 1156, 918 cm$^{-1}$; MS (ESI): m/z 327.1 [M+Na]$^+$.

Example 5

N-methyl-N-(naphthalen-1-ylmethyl)prop-2-en-1-amine (5f)

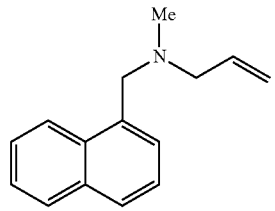 [SMILES: C=CCN(C)Cc1cccc2ccccc12]

83% yield; H NMR (400 MHz, CDCl$_3$) δ 8.33 (d, J=8.1 Hz, 1H), 7.88 (d, J=7.7 Hz, 1H), 7.81 (d, J=7.4 Hz, 1H), 7.57-7.41 (m, 4H), 6.08-5.99 (m, 1H), 5.31-5.21 (m, 2H), 3.93 (s, 2H), 3.16 (d, J=6.2 Hz, 2H), 2.26 (s, 3H); C NMR (100 MHz, CDCl$_3$) δ 135.9, 134.9, 133.8, 132.5, 128.4, 127.8, 127.4, 125.8, 125.5, 125.1, 124.6, 117.6, 61.2, 59.9, 42.3; IR (neat): ν=2784, 1509, 1451, 1020, 995, 918 cm$^{-1}$; MS (ESI): m/z 234.1 [M+Na]$^+$.

Example 6 methyl 4-(allyl(4-fluorobenzyl)amino)butanoate (5g)

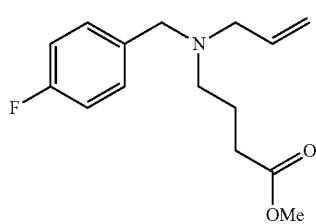 [SMILES: C=CCN(CCCC(=O)OC)Cc1ccc(F)cc1]

50% yield; H NMR (400 MHz, CDCl$_3$) δ 7.27-7.24 (m, 2H), 6.97 (t, J=8.5 Hz, 2H), 5.88-5.78 (m, 1H), 5.18-5.10 (m, 2H), 3.63 (s, 3H), 3.50 (s, 2H), 3.03 (d, J=6.0 Hz, 2H), 2.42 (t, J=6.8 Hz, 2H), 2.31 (t, J=7.3 Hz, 2H), 1.81-1.74 (m, 2H); C NMR (100 MHz, CDCl$_3$) δ 174.0, 161.7 (d, $J_{C-F}$=244.5 Hz), 135.7, 135.2, 130.1 (d, $J_{C-F}$=7.8 Hz), 117.3, 114.8 (d, $J_{C-F}$=21.2 Hz), 57.2, 56.4, 52.1, 51.3, 31.6, 22.3; F NMR (376 MHz, CDCl$_3$) δ −117.9; IR (neat): ν=1736, 1508, 1436, 1240, 1172, 1154 cm$^{-1}$; MS (ESI): m/z 288.1 [M+Na]$^+$.

Example 7

1-allyl-4-tosyl-1,4-diazepane (5h)

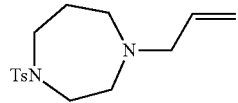

88% yield; H NMR (400 MHz, CDCl$_3$) δ 7.64 (d, J=7.9 Hz, 2H), 7.27 (d, J=8.0 Hz, 2H), 5.82-5.72 (m, 1H), 5.14-5.08 (m, 2H), 3.34-3.33 (m, 4H), 3.06 (d, J=6.1 Hz, 2H), 2.66-2.61 (m, 4H), 2.40 (s, 3H), 1.80-1.78 (m, 2H); C NMR (100 MHz, CDCl$_3$) δ 143.0, 136.0, 135.4, 129.6, 126.9, 117.6, 60.9, 55.7, 54.0, 48.2, 46.9, 27.8, 21.4; IR (neat): ν=1332, 1155, 1090, 994, 919, 895 cm$^{-1}$; MS (ESI): m/z 317.1 [M+Na]$^+$.

Example 8

3-allyl-8-methoxy-1-phenyl-2,3,4,5-tetrahydro-1H-benzo[d]azepine (5j)

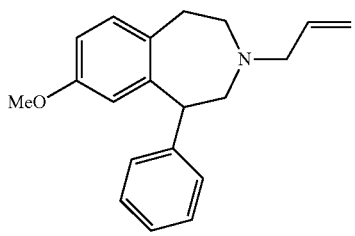 [SMILES: C=CCN1CCc2ccc(OC)cc2C(c2ccccc2)C1]

76% yield; H NMR (400 MHz, CDCl$_3$) δ 7.38-7.19 (m, 5H), 7.07 (d, J=8.1 Hz, 1H), 6.67 (d, J=7.2 Hz, 1H), 6.29 (s, 1H), 5.97-5.87 (m, 1H), 5.21-5.14 (m, 2H), 4.33 (d, J=8.1 Hz, 1H), 3.67 (s, 3H), 3.22-2.92 (m, 6H), 2.85-2.80 (m, 1H), 2.46-2.42 (m, 1H); C NMR (100 MHz, CDCl$_3$) δ 157.9, 145.9, 143.0, 135.4, 133.7, 130.3, 128.5, 128.4, 126.3, 117.8, 115.1, 110.1, 62.6, 60.4, 55.5, 54.9, 50.1, 35.5; IR (neat): ν=1607, 1494, 1265, 1044, 994, 920 cm$^{-1}$; MS (ESI): m/z 316.2 [M+Na]$^+$.

Example 9

3-allyl-1-(4-bromophenyl)-8-methoxy-2,3,4,5-tetrahydro-1H-benzo[d]azepine (5k)

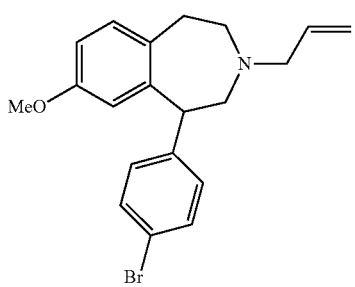 [SMILES: C=CCN1CCc2ccc(OC)cc2C(c2ccc(Br)cc2)C1]

86% yield; H NMR (400 MHz, CDCl$_3$) δ 7.45 (d, J=8.3 Hz, 2H), 7.06-7.04 (m, 3H), 6.68-6.66 (m, 1H), 6.29 (s, 1H), 5.93-5.84 (m, 1H), 5.20-5.14 (m, 2H), 4.25-4.24 (m, 1H), 3.69 (s, 3H), 3.19-2.94 (m, 5H), 2.86-2.76 (m, 2H), 2.50-2.48 (m, 1H); C NMR (100 MHz, CDCl$_3$) δ 157.9, 145.0, 141.8, 135.3, 133.6, 131.5, 130.5, 130.1, 120.0, 117.9, 115.3, 110.3, 62.6, 59.8, 55.6, 55.0, 49.7, 35.5; IR (neat): ν=1609, 1488, 1264, 1249, 1044, 1010, 995 cm$^{-1}$; MS (ESI): m/z 394.1 [M+Na]$^+$.

Example 10

1-allyl-4-(bis(4-fluorophenyl)methyl)piperazine (5l)

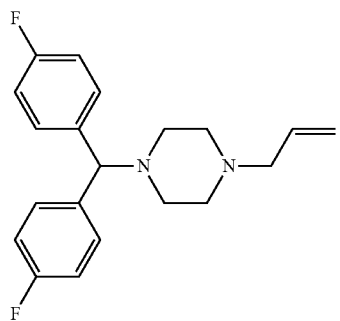 [SMILES: C=CCN1CCN(C(c2ccc(F)cc2)c2ccc(F)cc2)CC1]

74% yield; H NMR (400 MHz, CDCl$_3$) δ 7.36-7.32 (m, 4H), 6.99-6.93 (m, 4H), 5.90-5.80 (m, 1H), 5.19-5.11 (m, 2H), 4.22 (s, 1H), 3.00 (d, J=6.3 Hz, 2H), 7.46-7.41 (m, 8H); C NMR (100 MHz, CDCl$_3$) δ 161.7 (d, $J_{C-F}$=245.3 Hz), 138.2, 134.8, 129.2 (d, $J_{C-F}$=7.7 Hz), 117.9, 115.3 (d, $J_{C-F}$=21.2 Hz), 74.4, 61.6, 53.2, 51.6; F NMR (376 MHz, CDCl$_3$) δ −117.2; IR (neat): ν=1603, 1505, 1221, 1152, 1007, 825 cm$^{-1}$; MS (ESI): m/z 329.1 [M+H]$^+$.

Example 11

(E)-N-(2-(1H-indol-3-yl)ethyl)-N-benzyl-3-phenyl-prop-2-en-1-amine (7aa, Known Compound)

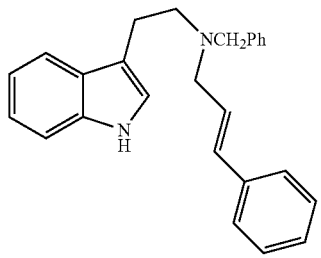

90% yield; H NMR (400 MHz, CDCl$_3$) δ 7.97 (br s, 1H), 7.55 (d, J=7.9 Hz, 1H), 7.43-7.19 (m, 12H), 7.11-7.07 (m, 1H), 6.97 (d, J=2.1 Hz, 1H), 6.60 (d, J=15.9 Hz, 1H), 6.38 (dt, J=15.9, 6.5 Hz, 1H), 3.83 (s, 2H), 3.44 (d, J=6.5 Hz, 2H), 3.08-3.04 (m, 2H), 2.96-2.93 (m, 2H); C NMR (100 MHz, CDCl$_3$) δ 139.8, 137.4, 136.4, 132.6, 129.2, 128.7, 128.4, 127.9, 127.7, 127.5, 127.1, 126.5, 122.0, 121.8, 119.3, 119.1, 114.6, 111.3, 58.6, 56.5, 54.3, 23.3.

Example 12

(E)-N-(2-(1H-indol-3-yl)ethyl)-N-benzyl-3-p-tolyl-prop-2-en-1-amine (7ab, Known Compound)

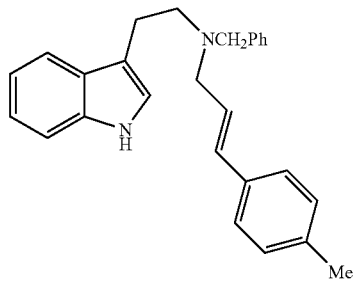

85% yield; H NMR (400 MHz, CDCl$_3$) δ 7.93 (br s, 1H), 7.54 (d, J=7.9 Hz, 1H), 7.43-7.08 (m, 12H), 6.96 (s, 1H), 6.56 (d, J=15.9 Hz, 1H), 6.31 (dt, J=15.8, 6.6 Hz, 1H), 3.80 (s, 2H), 3.40 (d, J=6.4 Hz, 2H), 3.05-3.01 (m, 2H), 2.92-2.90 (m, 2H), 2.37 (s, 3H); C NMR (100 MHz, CDCl$_3$) δ 139.8, 137.3, 136.4, 134.7, 132.5, 129.4, 129.2, 128.4, 127.8, 127.1, 126.8, 126.4, 122.1, 121.7, 119.4, 119.2, 114.8, 111.2, 58.6, 56.5, 54.3, 23.3, 21.4.

Example 13

(E)-N-(2-(1H-indol-3-yl)ethyl)-N-benzyl-3-m-tolyl-prop-2-en-1-amine (7ac, Known Compound)

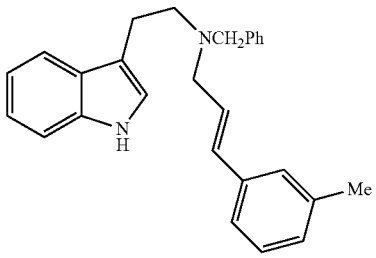

80%; H NMR (400 MHz, CDCl$_3$) δ 7.91 (br s, 1H), 7.52 (d, J=7.9 Hz, 1H), 7.42-7.18 (m, 10H), 7.07-7.04 (m, 2H), 6.98 (s, 1H), 6.54 (d, J=15.9 Hz, 1H), 6.33 (dt, J=15.8, 6.5 Hz, 1H), 3.78 (s, 2H), 3.39 (d, J=6.4 Hz, 2H), 3.04-3.00 (m, 2H), 2.92-2.89 (m, 2H), 2.36 (s, 3H); C NMR (100 MHz, CDCl$_3$) δ 139.8, 138.3, 137.4, 136.4, 132.7, 129.2, 128.7, 128.5, 128.3, 127.8, 127.3, 127.1, 123.7, 122.1, 121.8, 119.4, 119.2, 114.8, 111.3, 58.6, 56.5, 54.3, 23.3, 21.6.

Example 14

(E)-N-(2-(1H-indol-3-yl)ethyl)-N-benzyl-3-(4-iodophenyl)prop-2-en-1-amine (7ad)

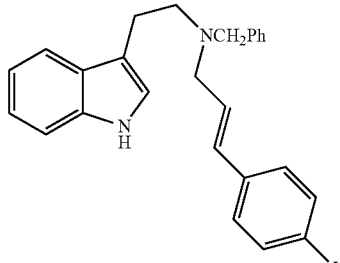

72% yield; H NMR (400 MHz, CDCl$_3$) δ 7.94 (br s, 1H), 7.64 (d, J=8.3 Hz, 2H), 7.52 (d, J=7.8 Hz, 1H), 7.42-7.28 (m, 7H), 7.19 (t, J=7.2 Hz, 1H), 7.08-7.05 (m, 3H), 6.97-6.96 (m, 1H), 6.47 (d, J=15.9 Hz, 1H), 6.31 (dt, J=15.9, 6.4 Hz, 1H), 3.78 (s, 2H), 3.37 (d, J=6.2 Hz, 2H), 3.04-3.00 (m, 2H), 2.93-2.89 (m, 2H); C NMR (100 MHz, CDCl$_3$) δ 139.7, 137.8, 137.0, 136.4, 131.4, 129.2, 128.5, 128.3, 127.8, 127.2, 126.5, 122.1, 121.8, 119.4, 119.1, 114.7, 111.3, 92.6, 58.7, 56.4, 54.4, 23.4; IR (neat): ν=3420, 2922, 2804, 1402, 1355, 1004, 969 cm$^{-1}$; MS (ESI): m/z 493.1 [M+H]$^+$.

Example 15

(E)-N-(2-(1H-indol-3-yl)ethyl)-N-benzyl-3-(4-fluorophenyl)prop-2-en-1-amine (7ae, Known Compound)

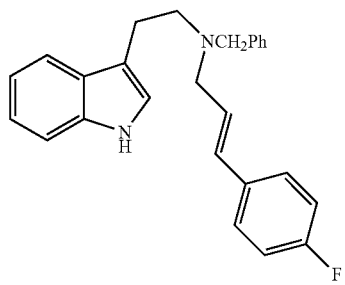

82% yield; H NMR (400 MHz, CDCl$_3$) δ 7.94 (br s, 1H), 7.52 (d, J=7.9 Hz, 1H), 7.37-7.26 (m, 8H), 7.19 (t, J=7.5 Hz, 1H), 7.08-6.97 (m, 4H), 6.52 (d, J=15.9 Hz, 1H), 6.23 (dt, J=15.8, 6.5 Hz, 1H), 3.79 (s, 2H), 3.38 (d, J=6.4 Hz, 2H), 3.04-3.00 (m, 2H), 2.93-2.89 (m, 2H); C NMR (100 MHz, CDCl$_3$) δ 162.4 (d, $J_{C-F}$=246.4 Hz), 139.8, 136.5, 133.6, 131.3, 129.2, 128.5, 128.0 (d, $J_{C-F}$=7.8 Hz), 127.8, 127.1, 122.1, 121.8, 119.4, 119.1, 115.6 (d, $J_{C-F}$=21.5 Hz), 114.8, 111.3, 58.6, 56.5, 54.4, 23.4; F NMR (376 MHz, CDCl$_3$) δ −116.52.

Example 16

(E)-N-(2-(1H-indol-3-yl)ethyl)-N-benzyl-3-(4-chlorophenyl)prop-2-en-1-amine (7af)

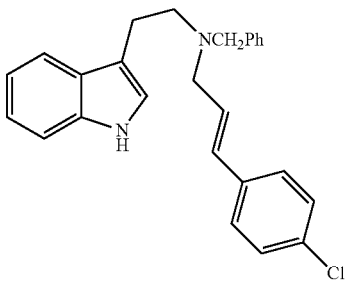

78% yield; H NMR (400 MHz, CDCl$_3$) δ 7.95 (br s, 1H), 7.54 (d, J=7.9 Hz, 1H), 7.44-7.19 (m, 11H), 7.08 (t, J=7.4 Hz, 1H), 6.96 (s, 1H), 6.51 (d, J=15.9 Hz, 1H), 6.30 (dt, J=15.9, 6.4 Hz, 1H), 3.80 (s, 2H), 3.39 (d, J=6.3 Hz, 2H), 3.06-3.02 (m, 2H), 2.94-2.90 (m, 2H); C NMR (100 MHz, CDCl$_3$) δ 139.7, 136.4, 135.9, 133.1, 131.2, 129.2, 128.9, 128.5, 127.7, 127.1, 122.1, 121.8, 119.4, 119.1, 114.7, 111.3, 58.7, 56.4, 54.4, 23.4; IR (neat): ν=3419, 2922, 2803, 1489, 1454, 1090, 1011, 970 cm$^{-1}$; MS (ESI): m/z 401.2 [M+H]$^+$.

Example 17

(E)-N-(2-(1H-indol-3-yl)ethyl)-N-benzyl-3-(4-bromophenyl)prop-2-en-1-amine (7ag)

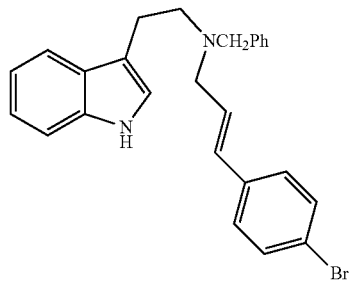

70%; H NMR (400 MHz, CDCl$_3$) δ 7.94 (br s, 1H), 7.53-7.17 (m, 12H), 7.06 (t, J=7.5 Hz, 1H), 6.96 (s, 1H), 6.48 (d, J=15.9 Hz, 1H), 6.30 (dt, J=15.9, 6.4 Hz, 1H), 3.78 (s, 2H), 3.36 (d, J=6.3 Hz, 2H), 3.04-3.00 (m, 2H), 2.92-2.88 (m, 2H); C NMR (100 MHz, CDCl$_3$) δ 139.7, 136.4, 131.8, 131.3, 129.2, 128.5, 128.0, 127.8, 127.2, 122.1, 121.8, 121.2, 119.4, 119.1, 114.7, 111.3, 58.7, 56.5, 54.4, 23.4; IR (neat): ν=3420, 2923, 2804, 1496, 1455, 1072, 1009, 970 cm$^{-1}$; MS (ESI): m/z 445.2 [M+H]$^+$.

Example 18

(E)-N-(2-(1H-indol-3-yl)ethyl)-N-benzyl-3-(4-(trifluoromethyl)phenyl)prop-2-en-1-amine (7ah, Known Compound)

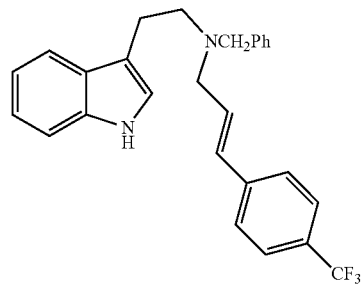

61% yield; H NMR (400 MHz, CDCl$_3$) δ 7.93 (br s, 1H), 7.53-7.50 (m, 3H), 7.44-7.25 (m, 8H), 7.18 (t, J=7.6 Hz, 1H), 7.05 (t, J=7.5 Hz, 1H), 6.98 (s, 1H), 6.56 (d, J=16.0 Hz, 1H), 6.39 (dt, J=15.9, 6.3 Hz, 1H), 3.78 (s, 2H), 3.39 (d, J=6.2 Hz, 2H), 3.04-3.00 (m, 2H), 2.92-2.89 (m, 2H); C NMR (100 MHz, CDCl$_3$) δ 140.9, 139.7, 136.5, 131.1, 129.2, 128.5, 127.8, 127.2, 126.6, 125.7, 122.2, 121.8, 119.4, 119.1, 114.8, 111.3, 58.8, 56.4, 54.5, 23.4; F NMR (376 MHz, CDCl$_3$) δ −63.95.

Example 19

(E)-ethyl 4-(3-((2-(1H-indol-3-yl)ethyl)(benzyl)amino)prop-1-enyl)benzoate (7ai)

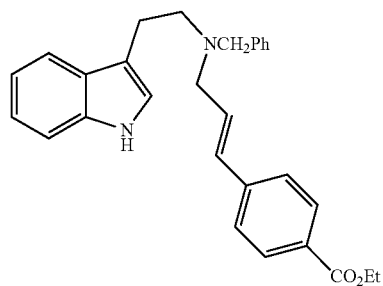

57% yield; H NMR (400 MHz, CDCl$_3$) δ 7.93-7.91 (m, 3H), 7.45 (d, J=7.9 Hz, 1H), 7.35-7.19 (m, 8H), 7.11 (t, J=7.6 Hz, 1H), 6.98 (t, J=7.5 Hz, 1H), 6.91-6.90 (m, 1H), 6.51 (d, J=16.0 Hz, 1H), 6.36 (dt, J=15.9, 6.3 Hz, 2H), 4.33 (q, J=7.1 Hz, 2H), 3.72 (s, 2H), 3.33 (d, J=6.0 Hz, 2H), 2.98-2.94 (m, 2H), 2.86-2.82 (m, 2H), 1.36 (t, J=7.1 Hz, 3H); C NMR (100 MHz, CDCl$_3$) δ 166.7, 141.8, 139.7, 136.5, 131.5, 131.1, 130.1, 129.3, 129.2, 128.5, 127.8, 127.2, 126.3, 122.1, 121.8, 119.4, 119.1, 114.7, 111.3, 61.1, 58.7, 56.5, 54.5, 23.4, 14.6; IR (neat): ν=3412, 2924, 2803, 1710, 1606, 1455, 1273, 1019, 972 cm$^{-1}$; (ESI): m/z 439.4 [M+H]$^+$.

Example 20

(E)-N-(2-(1H-indol-3-yl)ethyl)-N-(4-methoxybenzyl)-3-phenylprop-2-en-1-amine (7ba)

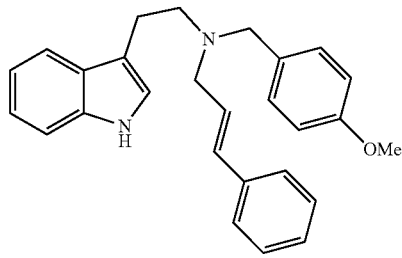 [SMILES: COc1ccc(CN(C/C=C/c2ccccc2)CCc2c[nH]c3ccccc23)cc1]

92% yield; H NMR (400 MHz, CDCl$_3$) δ 8.06 (br s, 1H), 7.52 (d, J=7.8 Hz, 1H), 7.39-7.20 (m, 8H), 7.20-7.16 (m, 1H), 7.06 (t, J=7.5 Hz, 1H), 6.97 (s, 1H), 6.89 (d, J=8.3 Hz, 2H), 6.57 (d, J=15.9 Hz, 1H), 6.35 (dt, J=15.8, 6.4 Hz, 1H), 3.82 (s, 3H), 3.76 (s, 2H), 3.41 (d, J=6.0 Hz, 2H), 3.06-3.02 (m, 2H), 2.93-2.90 (m, 2H); C NMR (100 MHz, CDCl$_3$) δ 158.6, 137.1, 136.2, 132.5, 130.3, 128.5, 127.5, 127.3, 126.3, 121.8, 121.5, 119.1, 118.9, 114.4, 113.6, 111.0, 57.6, 56.1, 55.2, 53.9, 22.9; IR (neat): ν=3420, 2925, 2834, 1611, 1511, 1455, 1247, 1033, 969 cm$^{-1}$; (ESI): m/z 397.4 [M+H]$^+$.

Example 21

(E)-N-(2-(1H-indol-3-yl)ethyl)-N-(4-fluorobenzyl)-3-phenylprop-2-en-1-amine (7bb)

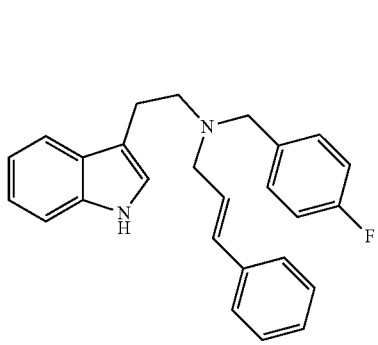 [SMILES: Fc1ccc(CN(C/C=C/c2ccccc2)CCc2c[nH]c3ccccc23)cc1]

78% yield; H NMR (400 MHz, CDCl$_3$) δ 7.92 (s, 1H), 7.52 (d, J=7.9 Hz, 1H), 7.39-7.17 (m, 9H), 7.09-6.96 (m, 4H), 6.57 (d, J=15.9 Hz, 1H), 6.33 (dt, J=15.8, 6.5 Hz, 1H), 3.73 (s, 2H), 3.38 (d, J=6.5 Hz, 2H), 3.03-2.99 (m, 2H), 2.91-2.87 (m, 2H); C NMR (100 MHz, CDCl$_3$) δ162.1 (d, J$_{C-F}$=244.5 Hz), 137.4, 136.5, 135.6, 132.7, 130.5 (d, J$_{C-F}$=7.7 Hz), 128.8, 127.9, 127.8, 127.6, 126.5, 122.1, 121.7, 119.4, 119.1, 115.2 (d, J$_{C-F}$=21.2 Hz), 114.8, 111.3, 57.82, 56.4, 54.3, 23.4; F NMR (376 MHz, CDCl$_3$) δ −117.76; IR (neat): ν=3420, 2922, 2809, 1407, 1455, 1220, 1090, 968 cm$^{-1}$; (ESI): m/z 385.3 [M+H]$^+$.

Example 22

(E)-N-(2-(1H-indol-3-yl)ethyl)-N-(4-nitrobenzyl)-3-phenylprop-2-en-1-amine (7bc)

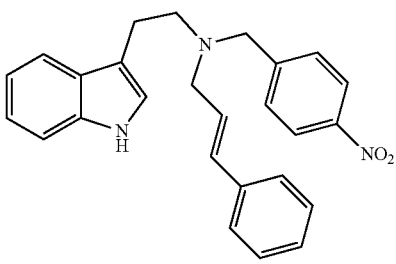 [SMILES: O=[N+]([O-])c1ccc(CN(C/C=C/c2ccccc2)CCc2c[nH]c3ccccc23)cc1]

56% yield; H NMR (400 MHz, CDCl$_3$) δ 8.11 (d, J=8.6 Hz, 2H), 7.95 (br s, 1H), 7.48 (d, J=8.0 Hz, 3H), 7.37-7.16 (m, 7H), 7.04 (t, J=7.4 Hz, 1H), 6.97 (s, 1H), 6.56 (d, J=15.9 Hz, 1H), 6.30 (dt, J=15.8, 6.5 Hz, 1H), 3.81 (s, 2H), 3.40 (d, J=6.2 Hz, 2H), 3.02-2.98 (m, 2H), 2.90-2.86 (m, 2H); C NMR (100 MHz, CDCl$_3$) δ 148.3, 147.2, 137.1, 136.5, 133.0, 129.4, 128.8, 127.8, 127.3, 126.5, 123.6, 122.2, 121.8, 119.5, 119.0, 114.5, 111.4, 58.0, 56.8, 54.7, 23.6; IR (neat): ν=3422, 2923, 2851, 1516, 1456, 1413, 1108, 969 cm$^{-1}$; (ESI): m/z 412.4 [M+H]$^+$.

Example 23

(E)-N-(2-(1H-indol-3-yl)ethyl)-N-(naphthalen-1-ylmethyl)-3-phenylprop-2-en-1-amine (7c, Known Compound)

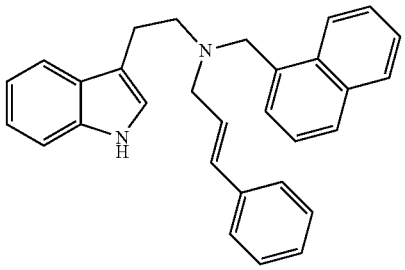 [SMILES: C(=C\c1ccccc1)/CN(CCc1c[nH]c2ccccc12)Cc1cccc2ccccc12]

70% yield; H NMR (400 MHz, CDCl$_3$) δ 8.37-8.35 (m, 1H), 7.88-7.78 (m, 3H), 7.56-7.15 (m, 12H), 7.04 (t, J=7.5 Hz, 1H), 6.91 (s, 1H), 6.59 (d, J=15.9 Hz, 1H), 6.39 (dt, J=15.8, 6.5 Hz, 1H), 4.19 (s, 2H), 3.44 (d, J=6.5 Hz, 2H), 3.09-2.97 (m, 4H); C NMR (100 MHz, CDCl$_3$) δ 137.5, 136.4, 135.5, 134.1, 132.7, 128.8, 128.6, 128.0, 127.8, 127.5, 126.5, 125.9, 125.8, 125.4, 125.0, 122.1, 121.8, 119.4, 119.2, 114.8, 111.2, 108.9, 57.2, 56.7, 54.7, 23.2.

Example 24

(E)-N-benzyl-N-(2-(1-methyl-1H-indol-3-yl)ethyl)-3-phenylprop-2-en-1-amine (7d)

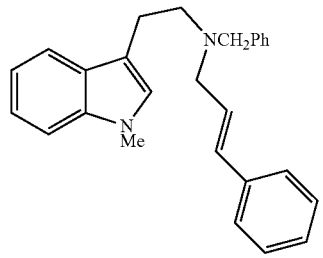

84% yield; H NMR (400 MHz, CDCl$_3$) δ 7.60 (d, J=7.9 Hz, 1H), 7.52-7.28 (m, 12H), 7.16-7.12 (m, 1H), 6.91 (s, 1H) 6.67 (d, J=15.9 Hz, 1H), 6.44 (dt, J=15.9, 6.5 Hz, 1H), 3.88 (s, 2H), 3.80 (s, 3H), 3.50 (d, J=6.4 Hz, 2H), 3.13-3.09 (m, 2H), 3.01-2.97 (m, 2H); C NMR (100 MHz, CDCl$_3$) δ 139.8, 137.4, 137.2, 132.7, 129.2, 128.8, 128.5, 128.2, 127.9, 127.5, 127.1, 126.6, 126.5, 121.6, 119.2, 118.8, 113.2, 109.3, 58.6, 56.5, 54.6, 32.7, 23.2; IR (neat): ν=3025, 2923, 2798, 1494, 1483, 1472, 1450, 1326, 1129, 968 cm$^{-1}$; (ESI): m/z 381.4 [M+H]$^+$.

Example 25

(E)-N,N-dibenzyl-3-phenylprop-2-en-1-amine (7e, Known Compound)

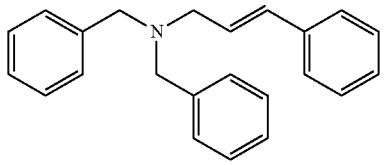 [SMILES: C(=C\c1ccccc1)/CN(Cc1ccccc1)Cc1ccccc1]

61% yield; H NMR (400 MHz, CDCl$_3$) δ 7.40-7.18 (m, 15H), 6.52 (d, J=15.9 Hz, 1H), 6.33-6.25 (m, 1H), 3.62 (s, 4H), 3.21 (d, J=6.2 Hz, 2H); C NMR (100 MHz, CDCl$_3$) δ 139.8, 137.4, 132.6, 128.9, 128.6, 128.3, 127.9, 127.4, 127.0, 126.4, 58.1, 55.9.

Example 26

(E)-N-methyl-N-(naphthalen-1-ylmethyl)-3-p-tolyl-prop-2-en-1-amine (7fa, Known Compound)

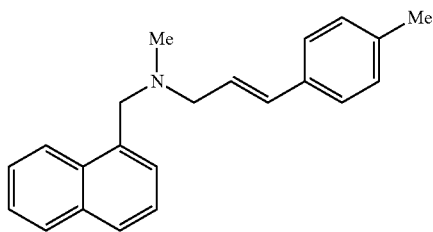 [SMILES: Cc1ccc(/C=C/CN(C)Cc2cccc3ccccc23)cc1]

83% yield; H NMR (400 MHz, CDCl$_3$) δ 8.33 (d, J=8.2 Hz, 1H), 7.87 (d, J=8.1 Hz, 1H), 7.80 (d, J=7.9 Hz, 1H), 7.56-7.41 (m, 4H), 7.32 (d, J=7.9 Hz, 2H), 7.14 (d, J=7.8 Hz, 2H), 6.57 (d, J=15.8 Hz, 1H), 6.35 (dt, J=15.7, 6.6 Hz, 1H), 3.97 (s, 2H), 3.30 (d, J=6.5 Hz, 2H), 2.36 (s, 3H), 2.30 (s, 3H); C NMR (100 MHz, CDCl$_3$) δ 137.4, 135.2, 134.7, 134.2, 132.8, 129.5, 128.7, 128.1, 127.7, 126.8, 126.5, 126.1, 125.8, 125.3, 124.9, 60.7, 60.3, 42.7, 21.4.

Example 27

(E)-N-methyl-N-(naphthalen-1-ylmethyl)-3-m-tolyl-prop-2-en-1-amine (7fb)

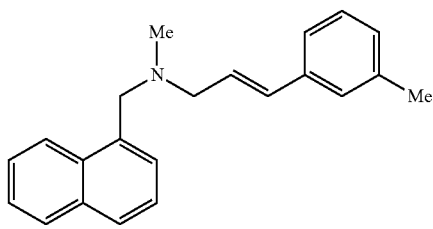 [SMILES: Cc1cccc(/C=C/CN(C)Cc2cccc3ccccc23)c1]

81% yield; H NMR (400 MHz, CDCl$_3$) δ 8.34 (d, J=8.3 Hz, 1H), 7.87 (d, J=7.9 Hz, 1H), 7.80 (d, J=7.9 Hz, 1H), 7.57-7.41 (m, 4H), 7.26-7.22 (m, 3H), 7.07 (s, 1H), 6.57 (d, J=15.9 Hz, 1H), 6.39 (dt, J=13.6, 6.6 Hz, 1H), 3.97 (s, 2H), 3.30 (d, J=6.5 Hz, 2H), 2.37 (s, 3H), 2.30 (s, 3H); C NMR (100 MHz, CDCl$_3$) δ 138.3, 137.4, 135.2, 134.1, 133.0, 132.8, 128.7, 128.4, 128.2, 127.7, 127.3, 126.1, 125.8, 125.4, 124.9, 123.7, 60.6, 60.3, 42.7, 21.6; IR (neat): ν=2922, 2785, 1415, 1361, 1016, 966 cm$^{-1}$; (ESI): m/z 302.3 [M+H]$^+$.

Example 28

(E)-N-methyl-N-(naphthalen-1-ylmethyl)-3-o-tolyl-prop-2-en-1-amine (7fc)

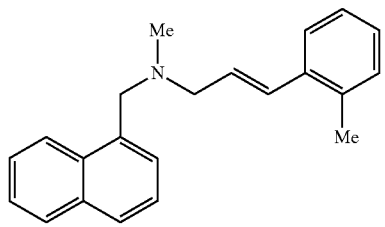 [SMILES: Cc1ccccc1/C=C/CN(C)Cc1cccc2ccccc12]

43% yield; H NMR (400 MHz, CDCl$_3$) δ 8.34 (d, J=8.2 Hz, 1H), 7.87 (d, J=7.9 Hz, 1H), 7.80 (d, J=8.0 Hz, 1H), 7.57-7.41 (m, 5H), 7.18 (d, J=7.9 Hz, 3H), 6.81 (d, J=15.7 Hz, 1H), 6.28 (dt, J=15.7, 6.6 Hz, 1H), 3.99 (s, 2H), 3.33 (d, J=6.6 Hz, 2H), 2.37 (s, 3H), 2.32 (s, 3H); C NMR (100 MHz, CDCl$_3$) δ 136.6, 135.5, 135.1, 134.1, 132.8, 130.9, 130.5, 129.1, 128.7, 128.2, 127.7, 127.5, 126.3, 126.1, 126.0, 125.8, 125.3, 124.9, 60.8, 60.2, 42.7, 20.1; IR (neat): ν=2924, 2785, 1459, 1362, 1014, 967 cm$^{-1}$; (ESI): m/z 302.3 [M+H]$^+$.

Example 29

(E)-3-(4-iodophenyl)-N-methyl-N-(naphthalen-1-ylmethyl)prop-2-en-1-amine (7fd)

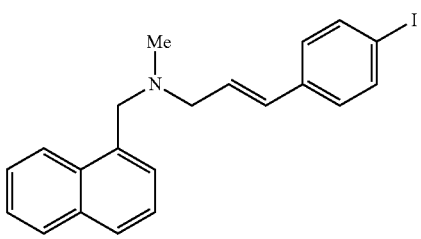 [SMILES: CN(C/C=C/c1ccc(I)cc1)Cc1cccc2ccccc12]

72% yield; H NMR (400 MHz, CDCl$_3$) δ 8.30 (d, J=8.1 Hz, 1H), 7.86 (d, J=7.9 Hz, 1H), 7.79 (d, J=7.8 Hz, 1H), 7.63 (d, J=8.2 Hz, 2H), 7.55-7.40 (m, 4H), 7.12 (d, J=8.1 Hz, 2H), 6.49 (d, J=15.9 Hz, 1H), 6.36 (dt, J=13.2, 6.4 Hz, 1H), 3.95 (s, 2H), 3.27 (d, J=6.4 Hz, 2H), 2.29 (s, 3H); C NMR (100 MHz, CDCl$_3$) δ 137.8, 136.9, 135.0, 134.1, 132.7, 131.7, 129.0, 128.7, 128.3, 128.2, 127.7, 126.1, 125.8, 125.4, 124.8, 92.7, 60.4, 42.8; IR (neat): ν=2924, 2785, 1482, 1360, 1004, 968 cm$^{-1}$; (ESI): m/z 414.2 [M+H]$^+$.

Example 30

(E)-3-(4-fluorophenyl)-N-methyl-N-(naphthalen-1-ylmethyl)prop-2-en-1-amine (7fe, Known Compound)

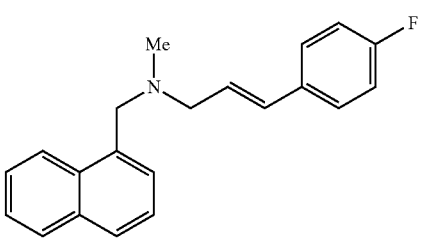 [SMILES: CN(C/C=C/c1ccc(F)cc1)Cc1cccc2ccccc12]

85% yield; H NMR (400 MHz, CDCl$_3$) δ 8.32 (d, J=8.2 Hz, 1H), 7.87 (d, J=7.7 Hz, 1H), 7.79 (d, J=7.9 Hz, 1H), 7.54-7.33 (m, 6H), 7.03-6.99 (m, 2H), 6.54 (d, J=15.9 Hz, 1H), 6.29 (dt, J=15.8, 6.6 Hz, 1H), 3.96 (s, 2H), 3.28 (d, J=6.4 Hz, 2H), 2.29 (s, 3H); C NMR (100 MHz, CDCl$_3$) δ 162.4 (d, $J_{C-F}$=246.4 Hz), 135.1, 134.1, 133.6, 132.7, 131.7, 128.7, 128.2, 128.0 (d, $J_{C-F}$=7.9 Hz), 127.7, 126.1, 125.8, 125.4, 124.8, 115.7 (d, $J_{C-F}$=21.6 Hz), 60.5, 60.4, 42.7; F NMR (376 MHz, CDCl$_3$) δ −116.38.

Example 31

(E)-3-(4-chlorophenyl)-N-methyl-N-(naphthalen-1-ylmethyl)prop-2-en-1-amine (7ff, Known Compound)

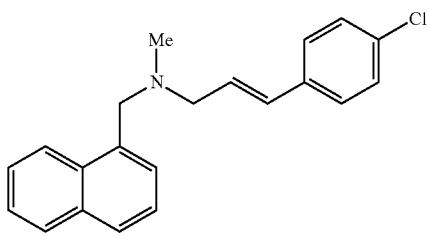 [SMILES: CN(C/C=C/c1ccc(Cl)cc1)Cc1cccc2ccccc12]

88% yield; H NMR (400 MHz, CDCl₃) δ 8.25 (d, J=8.0 Hz, 1H), 7.80 (d, J=7.8 Hz, 1H), 7.73 (d, J=7.8 Hz, 1H), 7.50-7.19 (m, 8H), 6.47 (d, J=15.9 Hz, 1H), 6.28 (dt, J=15.8, 6.6 Hz, 1H), 3.90 (s, 2H), 3.22 (d, J=6.5 Hz, 2H), 2.23 (s, 3H); C NMR (100 MHz, CDCl₃) δ 135.9, 135.0, 134.1, 133.2, 132.7, 131.6, 128.9, 128.7, 128.2, 127.7, 126.1, 125.8, 125.3, 124.8, 60.4, 42.74.

Example 32

(E)-3-(4-bromophenyl)-N-methyl-N-(naphthalen-1-ylmethyl)prop-2-en-1-amine (7fg)

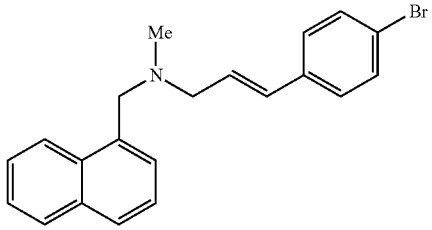 [SMILES: CN(C/C=C/c1ccc(Br)cc1)Cc1cccc2ccccc12]

84% yield; H NMR (400 MHz, CDCl₃) δ 8.16 (d, J=8.2 Hz, 1H), 7.72 (d, J=7.8 Hz, 1H), 7.65 (d, J=7.9 Hz, 1H), 7.41-7.28 (m, 6H), 7.10 (d, J=8.4 Hz, 2H), 6.37 (d, J=15.9 Hz, 1H), 6.21 (dt, J=15.8, 6.5 Hz, 1H), 3.82 (s, 2H), 3.13 (d, J=6.4 Hz, 2H), 2.15 (s, 3H); C NMR (100 MHz, CDCl₃) δ 136.3, 134.9, 134.1, 132.7, 131.9, 131.7, 128.7, 128.3, 128.1, 127.7, 126.1, 125.8, 125.4, 124.8, 121.3, 60.39, 42.70; IR (neat): ν=2924, 2786, 1486, 1071, 1008, 969 cm⁻¹; (ESI): m/z 366.3[M+H]⁺.

Example 33

(E)-N-methyl-N-(naphthalen-1-ylmethyl)-3-(4-(trifluoromethyl)phenyl)prop-2-en-1-amine (7fh)

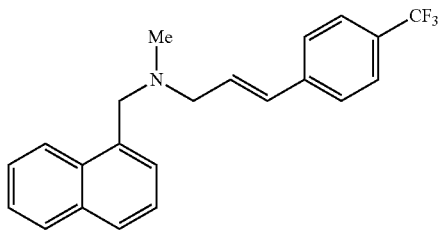 [SMILES: CN(C/C=C/c1ccc(C(F)(F)F)cc1)Cc1cccc2ccccc12]

77% yield; H NMR (400 MHz, CDCl₃) δ 8.32 (d, J=8.2 Hz, 1H), 7.87 (d, J=7.9 Hz, 1H), 7.80 (d, J=7.9 Hz, 1H), 7.58-7.42 (m, 8H), 6.61 (d, J=15.9 Hz, 1H), 6.46 (dt, J=15.9, 6.3 Hz, 1H), 3.98 (s, 2H), 3.31 (d, J=6.3 Hz, 2H), 2.31 (s, 3H); C NMR (100 MHz, CDCl₃) δ 140.8, 135.0, 134.2, 132.7, 131.3, 130.9, 129.5, 128.7, 128.3, 127.7, 126.6, 126.1, 125.9, 125.7 (q, $J_{C-F}$=3.4 Hz), 125.4, 124.8, 60.6, 60.3, 42.8; F NMR (376 MHz, CDCl₃) δ −63.96; IR (neat): ν=2789, 1424, 1120, 1109, 1067, 970 cm⁻¹; (ESI): m/z 356.3 [M+H]⁺.

Example 34

(E)-ethyl 4-(3-(methyl(naphthalen-1-ylmethyl)amino)prop-1-enyl)benzoate (7fi)

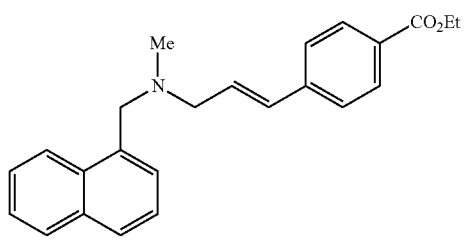 [SMILES: CCOC(=O)c1ccc(/C=C/CN(C)Cc2cccc3ccccc23)cc1]

86% yield; H NMR (400 MHz, CDCl₃) δ 8.31 (d, J=8.1 Hz, 1H), 7.99 (d, J=8.3 Hz, 2H), 7.86 (d, J=7.8 Hz, 1H), 7.79 (d, J=7.9 Hz, 1H), 7.54-7.40 (m, 6H), 6.61 (d, J=15.9 Hz, 1H), 6.47 (dt, J=15.9, 6.4 Hz, 1H), 4.38 (q, J=7.1 Hz, 2H), 3.97 (s, 2H), 3.30 (d, J=6.2 Hz, 2H), 2.31 (s, 3H), 1.40 (t, J=7.1 Hz, 3H); C NMR (100 MHz, CDCl₃) δ 166.6, 141.7, 134.8, 134.1, 132.7, 131.9, 130.7, 130.1, 129.4, 128.7, 128.3, 127.7, 126.3, 126.1, 125.8, 125.3, 124.8, 61.1, 60.5, 60.4, 42.8, 29.9, 14.6; IR (neat): ν=2928, 2787, 1713, 1273, 1177, 1105, 1105, 1019, 971 cm⁻¹; (ESI): m/z 360.4 [M+H]⁺.

Example 35

(E)-3-(4-methoxyphenyl)-N-methyl-N-(naphthalen-1-ylmethyl)prop-2-en-1-amine (7fj, Known Compound)

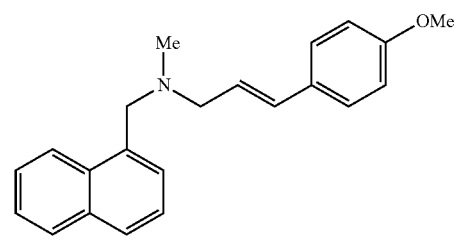 [SMILES: COc1ccc(/C=C/CN(C)Cc2cccc3ccccc23)cc1]

65% yield; H NMR (400 MHz, CDCl₃) δ 8.31 (d, J=8.1 Hz, 1H), 7.85 (d, J=7.9 Hz, 1H), 7.78 (d, J=7.9 Hz, 1H), 7.55-7.40 (m, 4H), 7.34 (d, J=8.0 Hz, 2H), 6.86 (d, J=8.1 Hz, 2H), 6.53 (d, J=15.8 Hz, 1H), 6.24 (dt, J=15.8, 6.7 Hz, 1H), 3.95 (s, 2H), 3.81 (s, 3H), 3.27 (d, J=6.6 Hz, 2H), 2.27 (s, 3H); C NMR (100 MHz, CDCl₃) δ 159.3, 135.2, 134.1, 132.8, 132.4, 130.2, 128.7, 128.1, 127.7, 126.1, 125.8, 125.6, 125.3, 124.9, 114.2, 60.8, 60.3, 55.5, 42.7.

Example 36

(E)-3-(3,4-dimethoxyphenyl)-N-methyl-N-(naphthalen-1-ylmethyl)prop-2-en-1-amine (7fk)

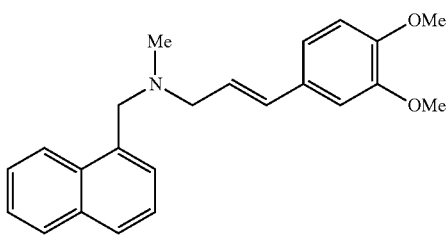 [SMILES: COc1ccc(/C=C/CN(C)Cc2cccc3ccccc23)cc1OC]

32% yield; H NMR (400 MHz, CDCl$_3$) δ 8.30 (d, J=8.2 Hz, 1H), 7.85 (d, J=7.6 Hz, 1H), 7.78 (d, J=8.0 Hz, 1H), 7.54-7.40 (m, 4H), 6.96-6.90 (m, 2H), 6.82 (d, J=8.2 Hz, 1H), 6.51 (d, J=15.8 Hz, 1H), 6.17 (dt, J=15.6, 6.6 Hz, 1H), 3.97 (s, 2H), 3.90 (s, 3H), 3.88 (s, 3H), 3.28 (d, J=6.5 Hz, 2H), 2.29 (s, 3H); C NMR (100 MHz, CDCl$_3$) δ 149.0, 148.6, 133.8, 132.4, 130.2, 128.4, 127.9, 127.4, 125.8, 125.5, 125.0, 124.5, 124.5, 119.4, 111.1, 108.7, 60.4, 60.0, 55.9, 55.7, 42.3; IR (neat): ν=2931, 2834, 1513, 1263, 1139, 1027, 967 cm$^{-1}$; (ESI): m/z 348.3 [M+H]$^+$.

Example 37

(E)-N-methyl-N-(naphthalen-1-ylmethyl)-3-(3-nitrophenyl)prop-2-en-1-amine (7fl)

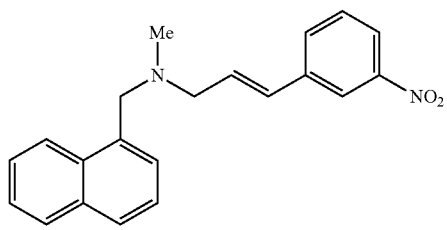 [SMILES: CN(C/C=C/c1cccc([N+](=O)[O-])c1)Cc1cccc2ccccc12]

53% yield; H NMR (400 MHz, CDCl$_3$) δ 8.31 (d, J=8.3 Hz, 1H), 8.21 (s, 1H), 8.06 (d, J=7.9 Hz, 1H), 7.86 (d, J=7.9 Hz, 1H), 7.79 (d, J=7.9 Hz, 1H), 7.64 (d, J=7.6 Hz, 1H), 7.57-7.40 (m, 5H), 6.61 (d, J=15.8 Hz, 1H), 6.48 (dt, J=15.8, 6.4 Hz, 1H), 3.98 (s, 2H), 3.30 (d, J=6.3 Hz, 2H), 2.32 (s, 3H); C NMR (100 MHz, CDCl$_3$) δ 148.8, 138.9, 134.1, 132.7, 132.3, 129.7, 128.8, 128.6, 128.1, 126.3, 126.07, 125.4, 124.6, 122.3, 121.2, 59.8, 42.6; IR (neat): ν=2924, 2788, 1527, 1461, 1349, 968 cm$^{-1}$; (ESI): m/z 332.3 [M+H]$^+$.

Example 38 methyl 4-(cinnamyl(4-fluorobenzyl)amino)butanoate (7ga)

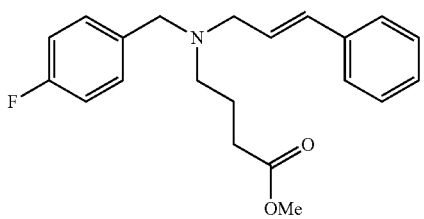 [SMILES: COC(=O)CCCN(C/C=C/c1ccccc1)Cc1ccc(F)cc1]

73% yield; H NMR (400 MHz, CDCl$_3$) δ 7.38-7.21 (m, 7H), 7.02-6.98 (m, 2H), 6.51 (d, J=15.9 Hz, 1H), 6.24 (dt, J=15.9, 6.6 Hz, 1H), 3.62 (s, 3H), 3.57 (s, 2H), 3.21 (d, J=6.4 Hz, 2H), 2.49 (t, J=6.9 Hz, 2H), 2.35 (t, J=7.4 Hz, 2H), 1.86-1.80 (m, 2H); C NMR (100 MHz, CDCl$_3$) δ 174.3, 162.1 (d, J$_{C-F}$=244.5 Hz), 137.3, 135.5, 132.8, 130.5 (d, J$_{C-F}$=7.6 Hz), 128.8, 127.6, 126.5, 115.2 (d, J$_{C-F}$=21.1 Hz), 57.7, 56.1, 52.6, 51.7, 32.0, 22.7; F NMR (376 MHz, CDCl$_3$) δ −117.62; IR (neat): ν=2927, 1785, 1508, 1220, 1171, 968 cm$^{-1}$; (ESI): m/z 342.4 [M+H]$^+$.

Example 39

(E)-methyl 4-((4-fluorobenzyl)(3-p-tolylallyl)amino)butanoate (7gb)

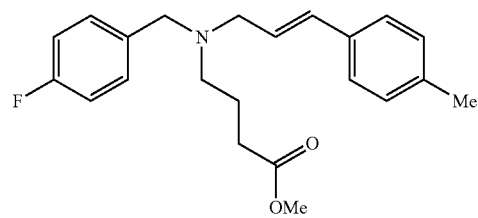 [SMILES: COC(=O)CCCN(C/C=C/c1ccc(C)cc1)Cc1ccc(F)cc1]

62% yield; H NMR (400 MHz, CDCl$_3$) δ 7.31-7.26 (m, 4H), 7.12 (d, J=7.9 Hz, 2H), 7.02-6.97 (m, 2H), 6.47 (d, J=15.9 Hz, 1H), 6.18 (dt, J=15.8, 6.6 Hz, 1H), 3.62 (s, 3H), 3.57 (s, 2H), 3.20 (d, J=6.4 Hz, 2H), 2.49 (t, J=6.9 Hz, 2H), 2.36-2.32 (m, 5H), 1.86-1.79 (m, 2H); C NMR (100 MHz, CDCl$_3$) δ 174.3, 162.1 (d, J$_{C-F}$=244.8 Hz), 137.4, 135.5, 134.6, 132.7, 130.5 (d, J$_{C-F}$=7.7 Hz), 129.5, 126.4, 115.2 (d, J$_{C-F}$=21.2 Hz), 57.7, 56.2, 52.6, 51.7, 32.00, 22.7, 21.4; F NMR (376 MHz, CDCl$_3$) δ −117.82; IR (neat): ν=2928, 1786, 1508, 1220, 1171, 970 cm$^{-1}$; (ESI): m/z 356.4 [M+H]$^+$.

Example 40

(E)-methyl 4-((3-(4-chlorophenyl)allyl)(4-fluorobenzyl)amino)butanoate (7gc)

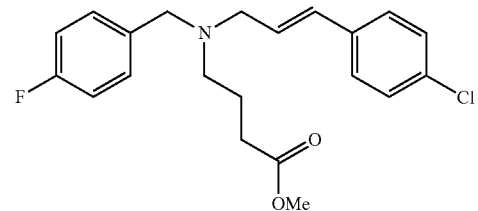 [SMILES: COC(=O)CCCN(C/C=C/c1ccc(Cl)cc1)Cc1ccc(F)cc1]

76% yield; H NMR (400 MHz, CDCl$_3$) δ 7.34-7.18 (m, 6H), 7.00 (t, J=8.7 Hz, 2H), 6.45 (d, J=15.9 Hz, 1H), 6.20 (dt, J=15.9, 6.5 Hz, 1H), 3.62 (s, 3H), 3.56 (s, 2H), 3.19 (d, J=5.8 Hz, 2H), 2.49 (t, J=6.9 Hz, 2H), 2.35 (t, J=7.3 Hz, 2H), 1.86-1.79 (m, 2H); C NMR (100 MHz, CDCl$_3$) δ 174.3, 162.1 (d, J$_{C-F}$=244.6 Hz), 135.8, 135.3, 133.2, 131.4, 130.5 (d, J$_{C-F}$=7.7 Hz), 128.9, 128.5, 127.7, 115.2 (d, J$_{C-F}$=21.1 Hz), 57.8, 56.1, 52.69, 51.7, 31.9, 22.7; F NMR (376 MHz, CDCl$_3$) δ −117.62; IR (neat): ν=2950, 1786, 1508, 1220, 1172, 1090, 970 cm$^{-1}$; (ESI): m/z 376.3 [M+H]$^+$.

Example 41

(E)-ethyl 4-(3-((4-fluorobenzyl)(4-methoxy-4-oxobutyl)amino)prop-1-enyl)benzoate (7gd)

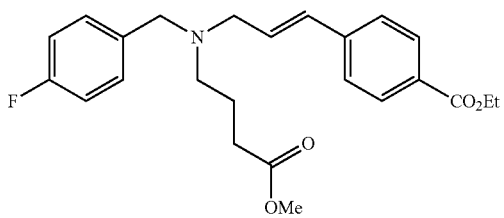 [SMILES: CCOC(=O)c1ccc(/C=C/CN(CCCC(=O)OC)Cc2ccc(F)cc2)cc1]

53% yield; H NMR (400 MHz, CDCl$_3$) δ 7.98 (d, J=8.3 Hz, 2H), 7.40 (d, J=8.3 Hz, 2H), 7.31-7.28 (m, 2H), 7.00 (t, J=8.6 Hz, 2H), 6.54 (d, J=16.0 Hz, 1H), 6.35 (dt, J=15.9, 6.4 Hz, 1H), 4.37 (q, J=7.1 Hz, 2H), 3.61 (s, 3H), 3.57 (s, 2H), 3.22 (d, J=6.1 Hz, 2H), 2.50 (t, J=6.8 Hz, 2H), 2.35 (t, J=7.3 Hz, 2H), 1.85-1.81 (m, 2H), 1.39 (t, J=7.1 Hz, 3H); C NMR (100 MHz, CDCl$_3$) δ 174.3, 162.2 (d, J$_{C-F}$=243.9 Hz), 161.0, 141.7, 135.3, 131.8, 130.7, 130.6, 130.5 (d, J$_{C-F}$=7.5 Hz), 130.1, 129.5, 126.3, 115.3 (d, J$_{C-F}$=21.2 Hz), 108.9, 61.1, 57.9, 56.1, 52.8, 51.7, 31.9, 22.7, 14.6; F NMR (376 MHz, CDCl$_3$) δ −117.62; IR (neat): ν=2951, 1735, 1713, 1508, 1171, 1273, 1220, 1176, 1106, 972 cm$^{-1}$; (ESI): m/z 414.4 [M+H]$^+$.

Example 42

1-cinnamyl-4-tosyl-1,4-diazepane (7ha)

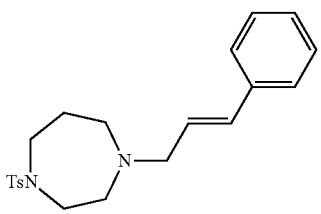 [SMILES: Cc1ccc(S(=O)(=O)N2CCCN(C/C=C/c3ccccc3)CC2)cc1]

81% yield; H NMR (400 MHz, CDCl$_3$) δ 7.67 (d, J=8.2 Hz, 2H), 7.43-7.22 (m, 7H), 6.49 (d, J=15.9 Hz, 1H), 6.20 (dt, J=15.8, 6.7 Hz, 1H), 3.39-3.36 (m, 4H), 3.25 (d, J=6.6 Hz, 2H), 2.75-2.69 (m, 4H), 2.42 (s, 3H), 1.87-1.81 (m, 2H); C NMR (100 MHz, CDCl$_3$) δ 143.3, 137.1, 136.4, 133.1, 129.9, 128.8, 127.8, 127.3, 126.5, 60.6, 56.2, 54.5, 48.5, 47.2, 28.2, 21.7; IR (neat): ν=2924, 1449, 1333, 1259, 1092, 970 cm$^{-1}$; (ESI): m/z 371.3 [M+H]$^+$.

Example 43

(E)-1-(3-p-tolylallyl)-4-tosyl-1,4-diazepane (7hb)

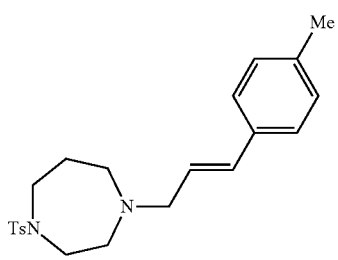 [SMILES: Cc1ccc(/C=C/CN2CCCN(S(=O)(=O)c3ccc(C)cc3)CC2)cc1]

77% yield; H NMR (400 MHz, CDCl$_3$) δ 7.67 (d, J=8.2 Hz, 2H), 7.30-7.24 (m, 4H), 7.11 (d, J=7.9 Hz, 2H), 6.45 (d, J=15.8 Hz, 1H), 6.14 (dt, J=15.8, 6.7 Hz, 1H), 3.39-3.35 (m, 4H), 3.24 (d, J=6.5 Hz, 2H), 2.79-2.65 (m, 4H), 2.42 (s, 3H), 2.33 (s, 3H), 1.86-1.83 (m, 2H); C NMR (100 MHz, CDCl$_3$) δ 143.3, 137.6, 136.4, 134.3, 133.0, 129.9, 129.5, 127.3, 126.4, 126.1, 60.7, 56.2, 54.5, 48.5, 47.3, 28.1, 21.7, 21.4; IR (neat): ν=2923, 1334, 1159, 1092, 972 cm$^{-1}$; (ESI): m/z 385.4 [M+H]$^+$.

Example 44

(E)-1-(3-(4-chlorophenyl)allyl)-4-tosyl-1,4-diazepane (7hc)

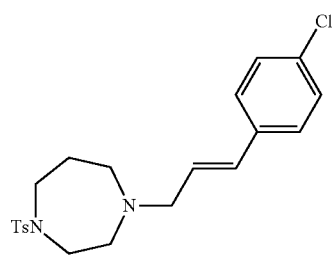 [SMILES: Cc1ccc(S(=O)(=O)N2CCCN(C/C=C/c3ccc(Cl)cc3)CC2)cc1]

81% yield; H NMR (400 MHz, CDCl$_3$) δ 7.66 (d, J=8.1 Hz, 2H), 7.30-7.26 (m, 6H), 6.43 (d, J=15.8 Hz, 1H), 6.17 (dt, J=15.8, 6.6 Hz, 1H), 3.37-3.34 (m, 4H), 3.24 (d, J=6.4 Hz, 2H), 2.73-2.68 (m, 4H), 2.41 (s, 3H), 1.85-1.82 (m, 2H); C NMR (100 MHz, CDCl$_3$) δ 143.3, 136.3, 135.5, 133.3, 131.8, 129.9, 128.9, 127.9, 127.7, 127.2, 60.4, 56.3, 54.5, 48.4, 47.2, 28.2, 21.7; IR (neat): ν=2924, 1491, 1333, 1159, 1091, 972 cm$^{-1}$; (ESI): m/z 405.3 [M+H]$^+$.

Example 45

3-cinnamyl-8-methoxy-1-phenyl-2,3,4,5-tetrahydro-1H-benzo[d]azepine (7ja)

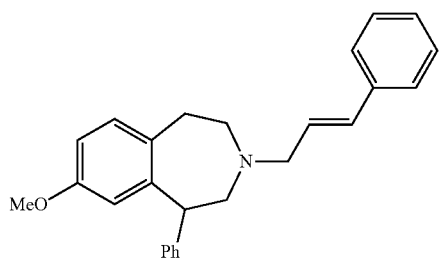 [SMILES: COc1ccc2c(c1)C(c1ccccc1)CN(C/C=C/c1ccccc1)CC2]

75% yield; H NMR (400 MHz, CDCl$_3$) δ 7.39-7.18 (m, 10H), 7.07 (d, J=8.1 Hz, 1H), 6.66 (d, J=8.0 Hz, 1H), 6.52 (d, J=15.8 Hz, 1H), 6.36-6.29 (m, 2H), 4.35 (d, J=7.9 Hz, 1H), 3.66 (s, 3H), 3.40-2.97 (m, 6H), 2.87-2.81 (m, 1H), 2.52-2.47 (m, 1H); C NMR (100 MHz, CDCl$_3$) δ 158.2, 146.0, 143.2, 137.2, 133.9, 133.0, 130.6, 128.8, 128.7, 127.7, 127.3, 126.6, 115.5, 110.6, 62.2, 61.0, 55.8, 55.3, 50.6, 35.9; IR (neat): ν=3025, 2932, 2807, 1495, 1263, 1044, 969 cm$^{-1}$; (ESI): m/z 370.4 [M+H]$^+$.

Example 46

(E)-8-methoxy-1-phenyl-3-(3-p-tolylallyl)-2,3,4,5-tetrahydro-1H-benzo[d]azepine (7jb)

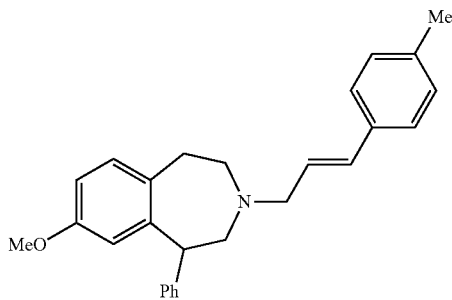 [SMILES: COc1ccc2c(c1)C(c1ccccc1)CN(C/C=C/c1ccc(C)cc1)CC2]

73% yield; H NMR (400 MHz, CDCl$_3$) δ 7.37-7.06 (m, 10H), 6.67-6.65 (m, 1H), 6.49 (d, J=15.8 Hz, 1H), 6.29-6.22 (m, 2H), 4.34 (d, J=8.0 Hz, 1H), 3.67 (s, 3H), 3.39-2.81 (m, 7H), 2.51-2.46 (m, 1H), 2.34 (s, 3H); C NMR (100 MHz, CDCl$_3$) δ 158.2, 146.1, 143.2, 137.5, 134.4, 134.0, 132.9, 130.6, 129.5, 128.7, 128.7, 126.6, 126.5, 126.2, 115.5, 110.5, 62.3, 60.9, 55.8, 55.3, 50.6, 35.9, 21.4; IR (neat): ν=3024, 2933, 2806, 1494, 1264, 1044, 971 cm$^{-1}$; (ESI): m/z 384.4 [M+H]$^+$.

Example 47

(E)-3-(3-(4-iodophenyl)allyl)-8-methoxy-1-phenyl-2,3,4,5-tetrahydro-1H-benzo[d]azepine (7jc)

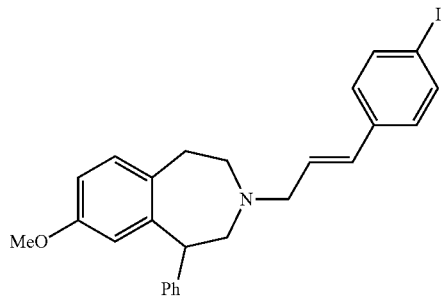 [SMILES: COc1ccc2c(c1)C(c1ccccc1)CN(C/C=C/c1ccc(I)cc1)CC2]

60% yield; H NMR (400 MHz, CDCl$_3$) δ 7.64 (d, J=8.3 Hz, 2H), 7.39-7.06 (m, 8H), 6.68-6.66 (m, 1H), 6.44 (d, J=15.9 Hz, 1H), 6.35-6.28 (m, 2H), 4.34 (d, J=7.9 Hz, 1H), 3.67 (s, 3H), 3.40-2.82 (m, 7H), 2.52-2.47 (m, 1H); C NMR (100 MHz, CDCl$_3$) δ 158.2, 145.9, 143.1, 137.8, 136.7, 133.8, 131.9, 130.6, 128.8, 128.6, 128.4, 128.3, 126.6, 115.5, 110.6, 92.8, 62.1, 61.0, 55.8, 55.3, 50.6, 35.9; IR (neat): ν=3025, 2933, 2807, 1495, 1264, 1003, 971 cm$^{-1}$; (ESI): m/z 496.3 [M+H]$^+$.

Example 48

(E)-3-(3-(4-fluorophenyl)allyl)-8-methoxy-1-phenyl-2,3,4,5-tetrahydro-1H-benzo[d]azepine (7jd)

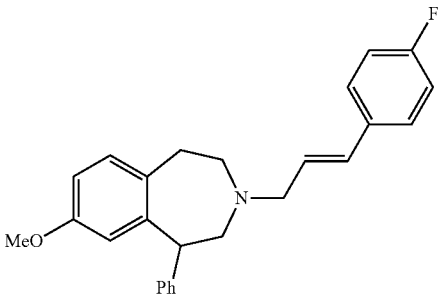 [SMILES: COc1ccc2c(c1)C(c1ccccc1)CN(C/C=C/c1ccc(F)cc1)CC2]

75% yield; H NMR (400 MHz, CDCl$_3$) δ 7.34-7.18 (m, 7H), 7.08-6.98 (m, 3H), 6.67 (d, J=8.1 Hz, 1H), 6.47 (d, J=15.8 Hz, 1H), 6.29-6.19 (m, 2H), 4.34 (d, J=7.8 Hz, 1H), 3.66 (s, 3H), 3.38-2.81 (m, 7H), 2.51-2.46 (m, 1H); C NMR (100 MHz, CDCl$_3$) δ 162.4 (d, J$_{C-F}$=246.5 Hz), 158.2, 146.0, 143.2, 133.9, 133.4, 131.8, 130.6, 128.8, 128.6, 128.0 (d, J$_{C-F}$=7.9 Hz), 127.1, 126.6, 115.7 (d, J$_{C-F}$=22.2 Hz), 110.5, 62.1, 61.0, 55.8, 55.3, 50.6, 35.9; F NMR (376 MHz, CDCl$_3$) δ −116.23; IR (neat): ν=3026, 2934, 2806, 1507, 1227, 1158, 970 cm$^{-1}$; (ESI): m/z 387.2 [M+H]$^+$.

Example 49

(E)-3-(3-(4-chlorophenyl)allyl)-8-methoxy-1-phenyl-2,3,4,5-tetrahydro-1H-benzo[d]azepine (7je)

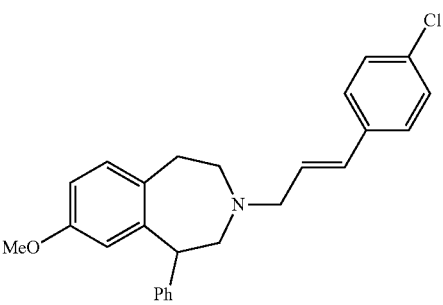 [SMILES: COc1ccc2c(c1)C(c1ccccc1)CN(C/C=C/c1ccc(Cl)cc1)CC2]

77% yield; H NMR (400 MHz, CDCl$_3$) δ 7.36-7.17 (m, 9H), 7.07 (d, J=8.0 Hz, 1H), 6.66 (d, J=8.1 Hz, 1H), 6.46 (d, J=15.8 Hz, 1H), 6.31-6.25 (m, 2H), 4.34 (d, J=7.8 Hz, 1H), 3.66 (s, 3H), 3.38-2.81 (m, 7H), 2.52-2.46 (m, 1H); C NMR (100 MHz, CDCl$_3$) δ 158.2, 146.0, 143.1, 135.7, 133.9, 133.2, 131.7, 130.6, 128.9, 128.8, 128.6, 128.1, 127.7, 126.6, 115.5, 110.5, 62.1, 61.0, 55.8, 55.3, 50.6, 35.9; IR (neat): ν=3026, 2935, 2807, 1491, 1264, 1090, 971 cm$^{-1}$; (ESI): m/z 404.4 [M+H]$^+$.

Example 50

(E)-8-methoxy-1-phenyl-3-(3-(4-(trifluoromethyl)phenyl)allyl)-2,3,4,5-tetrahydro-1H-benzo[d]azepine (7jf)

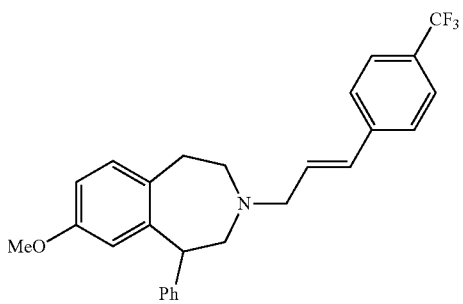 [SMILES: COc1ccc2c(c1)C(c1ccccc1)CN(C/C=C/c1ccc(C(F)(F)F)cc1)CC2]

66% yield; H NMR (400 MHz, CDCl$_3$) δ 7.59-7.06 (m, 10H), 6.67-6.65 (m, 1H), 6.54 (d, J=15.9 Hz, 1H), 6.43-6.37 (m, 1H), 6.29 (s, 1H), 4.34 (d, J=7.7 Hz, 1H), 3.66 (s, 3H), 3.40-2.82 (m, 7H), 2.53-2.48 (m, 1H); C NMR (100 MHz, CDCl$_3$) δ 158.2, 145.9, 143.1, 140.7, 133.8, 131.6, 130.6, 130.3, 128.8, 128.6, 126.7, 126.6, 125.8, 125.7, 115.6, 110.6, 62.0, 61.0, 55.9, 55.3, 50.6, 35.9; F NMR (376 MHz, CDCl$_3$) δ −64.00; IR (neat): ν=2934, 2807, 1613, 1423, 1162, 1120, 1066, 973 cm$^{-1}$; (ESI): m/z 438.4 [M+H]$^+$.

Example 51

(E)-1-(4-bromophenyl)-8-methoxy-3-(3-(4-(trifluoromethyl)phenyl)allyl)-2,3,4,5-tetrahydro-1H-benzo[d]azepine (7ka)

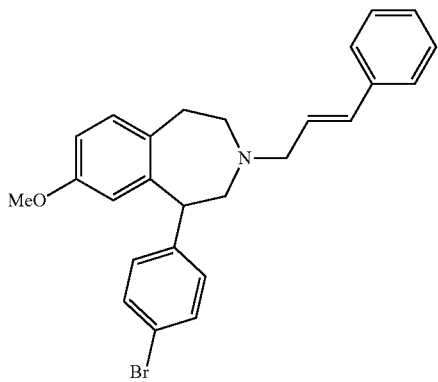 [SMILES: COc1ccc2c(c1)C(c1ccc(Br)cc1)CN(C/C=C/c1ccccc1)CC2]

81% yield; H NMR (400 MHz, CDCl$_3$) δ 7.49-7.22 (m, 10H), 6.70-6.67 (m, 1H), 6.52 (d, J=15.9 Hz, 1H), 6.34-6.26 (m, 2H), 4.27 (d, J=7.5 Hz, 1H), 3.70 (s, 3H), 3.38-2.79 (m, 7H), 2.58-2.53 (m, 1H); C NMR (100 MHz, CDCl$_3$) δ 158.3, 145.2, 142.1, 137.1, 133.9, 133.2, 131.8, 130.8, 130.4, 128.8, 127.7, 127.1, 126.5, 120.4, 115.7, 110.7, 62.3, 60.3, 55.9, 55.4, 50.2, 35.8; IR (neat): ν=3024, 2933, 2809, 1609, 1488, 1261, 1011, 969 cm$^{-1}$; (ESI): m/z 448.3 [M+H]$^+$.

Example 52

(E)-1-(4-bromophenyl)-8-methoxy-3-(3-p-tolylallyl)-2,3,4,5-tetrahydro-1H-benzo[d]azepine (7kb)

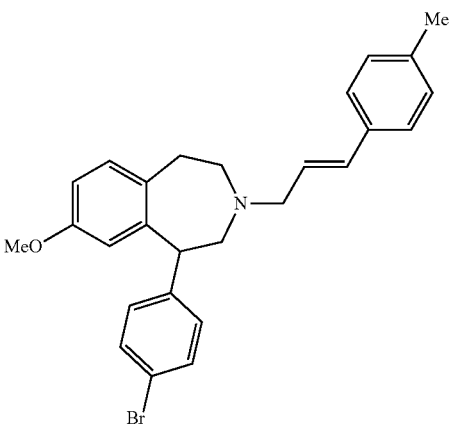 [SMILES: COc1ccc2c(c1)C(c1ccc(Br)cc1)CN(C/C=C/c1ccc(C)cc1)CC2]

70% yield; H NMR (400 MHz, CDCl$_3$) δ 7.45 (d, J=8.3 Hz, 2H), 7.27 (d, J=8.1 Hz, 2H), 7.14-7.04 (m, 5H), 6.69-6.66 (m, 1H), 6.48 (d, J=15.8 Hz, 1H), 6.30-6.20 (m, 2H), 4.26 (d, J=7.5 Hz, 1H), 3.70 (s, 3H), 3.36-2.77 (m, 7H), 2.58-2.51 (m, 1H), 2.34 (s, 3H); C NMR (100 MHz, CDCl$_3$) δ 158.2, 145.2, 142.1, 137.6, 134.4, 133.9, 133.1, 131.8, 130.8, 130.4, 129.5, 126.5, 126.0, 120.4, 115.7, 110.7, 62.3, 60.3, 55.9, 55.7, 50.2, 35.8, 21.4; IR (neat): ν=2930, 2808, 1609, 1500, 1487, 1262, 1011, 971 cm$^{-1}$; (ESI): m/z 462.3 [M+H]$^+$.

Example 53

(E)-1-(4-bromophenyl)-3-(3-(4-chlorophenyl)allyl)-8-methoxy-2,3,4,5-tetrahydro-1H-benzo[d]azepine (7kc)

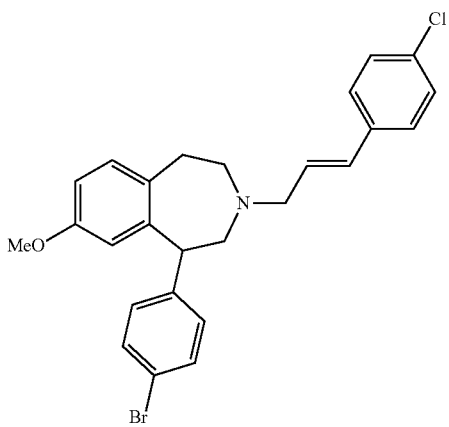 [SMILES: COc1ccc2c(c1)C(c1ccc(Br)cc1)CN(C/C=C/c1ccc(Cl)cc1)CC2]

81% yield; H NMR (400 MHz, CDCl$_3$) δ 7.45 (d, J=8.4 Hz, 2H), 7.30 (br s, 5H), 7.08-7.04 (m, 3H), 6.69-6.67 (m, 1H), 6.46 (d, J=15.9 Hz, 1H), 6.31-6.23 (m, 2H), 4.27 (d, J=7.3 Hz, 1H), 3.70 (s, 3H), 3.37-2.78 (m, 7H), 2.57-2.52 (m, 1H); C NMR (100 MHz, CDCl$_3$) δ 158.2, 145.1, 142.0, 135.6, 133.8, 133.3, 131.9, 131.8, 130.8, 130.3, 128.9, 127.8, 127.7, 120.4, 115.7, 110.7, 62.1, 60.4, 55.9, 55.3, 50.1, 35.8; IR (neat): ν=2938, 2811, 1608, 1488, 1261, 1090, 1011, 971 cm$^{-1}$; (ESI): m/z 482.3 [M+H]$^+$.

Example 54

(E)-N-methyl-N-(naphthalen-1-ylmethyl)-3-phenyl-prop-2-en-1-amine (Naftifine, 1, Known Compound)

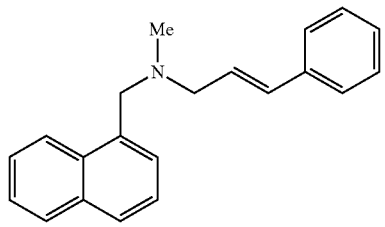 [SMILES: CN(C/C=C/c1ccccc1)Cc1cccc2ccccc12]

90% yield (72% for gram scale); H NMR (400 MHz, CDCl$_3$) δ 8.32 (d, J=8.2 Hz, 1H), 7.87 (d, J=7.7 Hz, 1H), 7.79 (d, J=8.0 Hz, 1H), 7.58-7.40 (m, 6H), 7.35-7.23 (m, 3H), 6.60 (d, J=15.9 Hz, 1H), 6.40 (dt, J=15.8, 6.6 Hz, 1H), 3.97 (s, 2H), 3.31 (d, J=6.6 Hz, 2H), 2.30 (s, 3H); C NMR (100 MHz, CDCl$_3$) δ 137.4, 135.1, 134.1, 132.9, 132.7, 128.8, 128.7, 128.2, 127.9, 127.7, 127.6, 126.6, 126.1, 125.8, 125.4, 124.9, 60.6, 60.3, 42.7.

Example 55

1-benzhydryl-4-cinnamylpiperazine (Cinnarizine, 2, Known Compound)

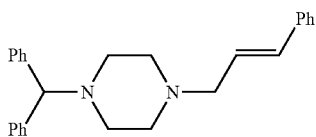

65% yield; H NMR (400 MHz, CDCl$_3$) δ 7.49-7.16 (m, 15H), 6.52 (d, J=15.8 Hz, 1H), 6.28 (dt, J=15.7, 6.8 Hz, 1H), 4.25 (s, 1H), 3.18 (d, J=6.8 Hz, 2H), 2.55-2.47 (m, 8H); C NMR (100 MHz, CDCl$_3$) δ 143.0, 137.2, 133.3, 128.8, 128.7, 128.2, 127.7, 127.1, 126.2, 126.5, 76.4, 61.3, 53.7, 52.1.

Example 56

1-(bis(4-fluorophenyl)methyl)-4-cinnamylpiperazine (Flunarizine, 3, Known Compound)

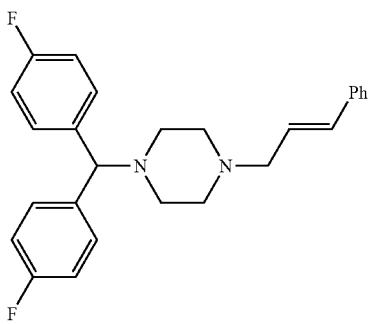 [SMILES: Fc1ccc(C(c2ccc(F)cc2)N2CCN(C/C=C/c3ccccc3)CC2)cc1]

55% yield; H NMR (400 MHz, CDCl$_3$) δ 7.34-7.20 (m, 9H), 6.96-6.94 (m, 4H), 6.51 (d, J=15.7 Hz, 1H), 6.26 (dt, J=14.6, 6.4 Hz, 1H), 4.23 (s, 1H), 3.17 (d, J=6.7 Hz, 2H), 2.53-2.42 (m, 8H); C NMR (100 MHz, CDCl$_3$) δ 162.0 (d, $J_{C-F}$=245.1 Hz), 138.5, 137.2, 133.4, 129.5 (d, $J_{C-F}$=7.8 Hz), 128.8, 127.7, 126.5, 115.6 (d, $J_{C-F}$=21.2 Hz), 74.7, 61.2, 53.6, 51.9; F NMR (376 MHz, CDCl$_3$) δ −117.89.

Example 57

(11)

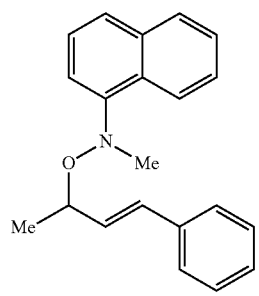

11

H NMR (400 MHz, CDCl$_3$) δ 7.97-7.79 (m, 3H), 7.49-7.24 (m, 9H), 5.92 (br s, 1H), 5.12-5.07 (m, 2H), 4.82-4.81 (m, 1H), 4.34-4.21 (m, 2H), 2.60 (s, 3H); C NMR (100 MHz, CDCl$_3$) δ 141.4, 138.5, 134.0, 133.4, 132.8, 128.8, 128.6, 128.4, 127.9, 126.0, 125.8, 125.4, 117.1, 85.1, 64.1, 46.1; IR (neat): ν=3033, 2847, 1511, 1453, 1020, 991, 926 cm$^{-1}$; (ESI): m/z 304.3 [M+H]$^+$.

Example 58

(12)

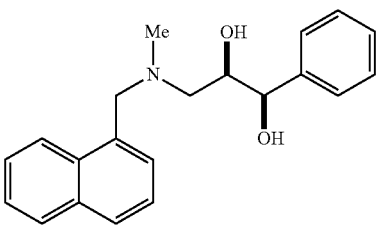

cis·12

H NMR (400 MHz, CDCl$_3$) δ 8.18 (d, J=8.0 Hz, 1H), 7.89-7.81 (m, 2H), 7.56-7.26 (m, 9H), 4.43-4.42 (m, 1H), 4.05-3.82 (m, 3H), 3.19 (br s, 2H), 2.72-2.66 (m, 1H), 2.31-2.28 (m, 4H); C NMR (100 MHz, CDCl$_3$) δ 140.9, 134.2, 134.0, 132.5, 129.0, 128.7, 128.6, 128.1, 126.9, 126.4, 126.0, 125.3, 124.2, 76.4, 71.5, 61.3, 59.7, 42.6; IR (neat): ν=3404, 2847, 1453, 1079, 1060, 1026 cm$^{-1}$; (ESI): m/z 322.4 [M+H]$^+$.

Example 59

(13)

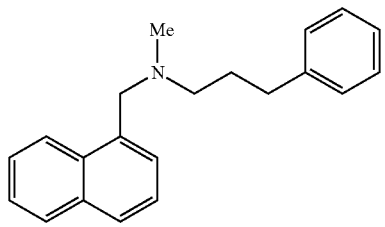

H NMR (400 MHz, CDCl$_3$) δ 8.36 (d, J=8.2 Hz, 1H), 7.90-7.80 (m, 2H), 7.57-7.15 (m, 9H), 3.93 (s, 2H), 2.67 (t, J=7.6 Hz, 2H), 2.55 (t, J=7.2 Hz, 2H), 2.26 (s, 3H), 1.93 (tt, J=7.6, 7.4 Hz, 2H); C NMR (100 MHz, CDCl$_3$) δ 142.7, 135.3, 134.1, 132.8, 128.7, 128.6, 128.5, 128.1, 127.6, 126.0, 125.9, 125.8, 125.4, 125.0, 61.2, 57.6, 42.5, 33.8, 29.4; IR (neat): ν=2942, 2788, 1495, 1453, 1017 cm$^{-1}$; (ESI): m/z 290.3 [M+H]$^+$.

Example 60

(14, Known Compound)

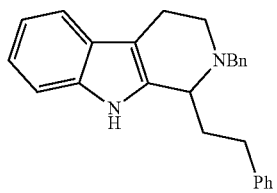

H NMR (400 MHz, CDCl$_3$) δ 7.54-7.10 (m, 14H), 3.84-3.77 (m, 2H), 3.71-3.68 (m, 1H), 3.34-3.27 (m, 1H), 3.04-2.59 (m, 5H), 2.20-1.99 (m, 2H); C NMR (100 MHz, CDCl$_3$) δ 142.7, 140.1, 136.1, 135.3, 129.3, 128.7, 128.7, 128.6, 127.6, 127.3, 126.0, 121.7, 119.6, 118.3, 110.9, 108.3, 57.6, 56.3, 44.8, 36.7, 32.6, 18.1.

Example 61

Compounds of the invention were evaluated for their ability to inhibit adenylyl cyclase activity. Adenylyl cyclases are enzymes that catalyze the production of cAMP from ATP. These enzymes are very important mediators of signaling through G protein-coupled receptors. There are nine different isoforms of membrane-bound adenylyl cyclases, each of which displays unique regulatory properties and expression patterns. Adenylyl cyclase type I (AC1) belongs to a family of adenylyl cyclases that are stimulated by calcium in a calmodulin-dependent manner. Notably, AC1 has been associated with chronic pain responses in several regions of the central nervous system. It has been previously shown that administration of NB001, a small molecule inhibitor of AC1 (IC$_{50}$=10 μM in cell models) leads to analgesic effects in both neuroinflammatory and neuropathic pain rodent models.

To determine whether compounds of the invention have an inhibitory effect on AC1 activity, HEK (human embryonic kidney) cells stably expressing AC1 (HEK-AC1) were employed and inhibition of Ca2+-stimulated cAMP accumulation was determined. A23187 is a Ca2+ ionophore, which promotes Ca2+ binding to calmodulin in the cells and, subsequent stimulation of AC1. Treatment of HEK-AC1 cells with A23187 led to a robust increase in cAMP accumulation consistent with Ca2+/calmodulin activation of AC1 (data not shown). Several of the compounds dose-dependently inhibited this cAMP response (See Table 1). These compounds displayed IC$_{50}$ values in the low M range, with the most potent being formula II, where X=p-BR, which had an IC$_{50}$ value of 6.91 (±0.50) M.

HEK (human embryonic kidney) cells stably expressing human AC1, were cultured in Dubelcco's Modified Eagle Medium (Life Technologies, Grand Island, N.Y.) supplemented with 5% bovine calf serum (Hyclone, Logan, Utah), 5% fetal clone I (Hyclone, Logan, Utah), Antibiotic-Antimycotic (Life Technologies, Grand Island, N.Y.), and G418 (Invivogen, San Diego, Calif.). The cells were grown to confluency in 15 cm disses, harvested using Cell Dissociation Buffer (Life Technologies, Grand Island, N.Y.), and resuspended in 4 ml of fetal bovine serum (Hyclone, Logan, Utah) containing 10% dimethyl sulfoxide (Sigma-Aldrich, St. Louis, Mo.). 1 ml of cell suspension was added to cryovials that were incubated overnight at −80° C. in a CoolCell device (BioCision, Larkspur, Calif.) for cryopreservation. On the following day, cryovials were stored in liquid N2 until the assay day.

Cryopreserved HEK-AC1 cells were thawed in a 37° C. water-bath, resuspended in 10 ml optiMEM (Life Technologies, Grand Island, N.Y.) and centrifuged at 500×g for 5 min. The cells were resuspended in 10 ml optiMEM and the centrifugation step was repeated. Cells were then resuspended in 1 ml optiMEM and counted using a Countess automated cell counter (Life Technologies, Grand Island, N.Y.). Cells were added to a white, flat bottom, low-volume, tissue culture-treated 384 well plate (PerkinElmer, Shelton, Conn.) at a final density of 2500 cells/well. The plate was centrifuged for 1 min at 100×g and incubated in a 37° C. humidified incubator for 1 h. Inhibitors of AC1 activity were added, the plate was centrifuged for 1 min at 100×g and incubated at room temperature for 30 min. Following this incubation A23187 (Sigma-Aldrich, St. Louis, Mo.) (3 μM final concentration) containing 3-isobutyl-1-methylxanthine (Sigma-Aldrich, St. Louis, Mo.) (0.5 mM final concentration) was added. The plate was centrifuged for 1 min at 100×g and incubated at room temperature for 1 h. Cyclic AMP accumulation was measured using Cisbio's dynamic 2 kit (Cisbio Bioassays, Bedford, Mass.) according to the manufacturer's instructions. Plates were analyzed for fluorescent emissions at 620 nm and 665 nm using 330 nm as the excitation wavelength in a Cytation 3 Cell Imaging Multi-Mode Reader (Biotek, Winooski, Vt.), and ratiometric analysis was carried out by dividing the 665 nm emissions by the 620 nm emissions to extrapolate the cAMP concentrations from a cAMP standard curve. The data represent the average of at least three independent experiments ran in duplicate.

Example 62

Several N,N-dialkylallylamines (5b, 5d, 5f, 5g, 5h, 5j, 5k, and 5l) were produced using the following general reaction:

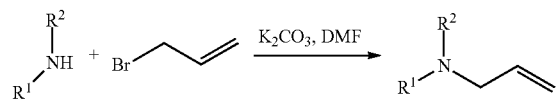

Under argon atmosphere, a mixture of a secondary amine (6 mmol) and K2CO3 (18 mmol) in DMF (20 mL) at room temperature was added allyl bromide (12 mmol). The reaction process was monitored by TLC. Upon full conversion of the starting amine, DCM (100 mL) and water was added to the reaction mixture. The organic layer was separated. The aqueous phase was further extracted with DCM three times. The combined organic extracts were washed with saturated aqueous NaCl for three times and dried over $Na_2SO_4$ and concentrated in vacuo. The residue was purified by column chromatography with a mixture of Hexane and EtOAc as eluent to afford the desire product.

Example 63

Heck reactions of N,N-dialkylallylamines were carried out following the following general reaction:

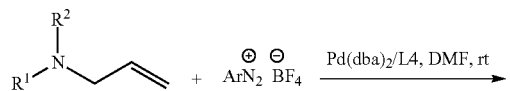

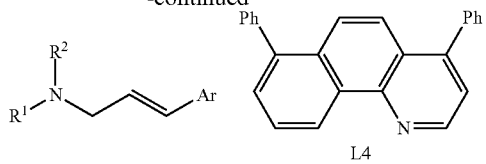

A mixture of $Pd(dba)_2$ (5.8 mg, 0.001 mmol) and L4 (4.0 mg, 0.0012 mmol) in DMF was stirred at room temperature for 20-30 min under argon. N,N-Dialkylallylamine and aryl diazonium salt were added to the reaction mixture. The reaction was stirred at room temperature for 12-16 h. Saturated sodium carbonate was added and the resulting mixture was stirred for 15-30 min. The organic layer was separated and extracted with EtOAc three times, and the combined organic extracts were washed with saturated aqueous NaCl three times and dried over $Na_2SO_4$ and concentrated in vacuo. The residue was purified by column chromatography (the silica gel was pretreated with $Et_3N$) with a mixture of Hexane and EtOAc as eluent to afford the desired product.

Conditions were optimized according to table 3:

TABLE 3

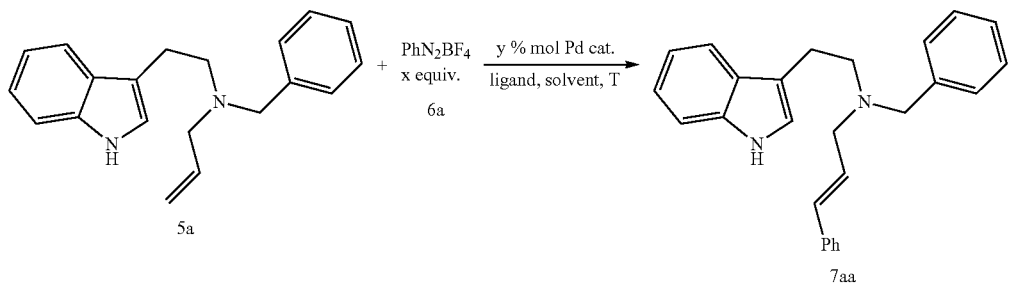 [SMILES: C=CCN(CCc1c[nH]c2ccccc12)CC1=C[C+]=CC=C1 ; C(=C\c1ccccc1)/CN(CCc1c[nH]c2ccccc12)Cc1ccccc1]

| entry | Pd cat. | y | solvent | ligand | base | x | T(° C.) | yield (%) |
|---|---|---|---|---|---|---|---|---|
| 1 | $Pd(dba)_2$ | 5 | DMF | L1 | — | 1.5 | rt | 54 |
| 2 | $Pd(dba)_2$ | 5 | PhMe | L1 | — | 1.5 | rt | — |
| 3 | $Pd(dba)_2$ | 5 | $CH_3CN$ | L1 | — | 1.5 | rt | — |
| 4 | $Pd(dba)_2$ | 5 | THF | L1 | — | 1.5 | rt | — |
| 5 | $Pd(dba)_2$ | 5 | DMA | L1 | — | 1.5 | rt | 33 |
| 6 | $Pd(dba)_2$ | 5 | DMSO | L1 | — | 1.5 | rt | trace |
| 7 | $Pd(dba)_2$ | 5 | DMF | L1 | — | 1.5 | 60 | 49 |
| 8 | $Pd(dba)_2$ | 5 | DMF | L1 | $Et_3N$ | 1.5 | rt | — |
| 9 | $Pd(dba)_2$ | 5 | DMF | L1 | $K_2CO_3$ | 1.5 | rt | — |
| 10 | $Pd(dba)_2$ | 5 | DMF | L1 | — | 2.0 | rt | 73 |
| 11 | $Pd(dba)_2$ | 5 | DMF | L1 | — | 2.5 | rt | 71 |
| 12 | $Pd(dba)_2$ | 8 | DMF | L1 | — | 2.0 | rt | 80 |
| 13 | $Pd(dba)_2$ | 10 | DMF | L1 | — | 2.0 | rt | 85 |
| 14 | $Pd(dba)_2$ | 10 | DMF | L2 | — | 2.5 | rt | 81 |
| 15 | $Pd(dba)_2$ | 10 | DMF | L3 | — | 2.0 | rt | 54 |
| 16 | $Pd(dba)_2$ | 10 | DMF | L4 | — | 2.0 | rt | 90 |
| 18 | $Pd(dba)_2$ | 10 | DMF | L5 | — | 2.0 | rt | 40 |
| 19 | $Pd(dba)_2$ | 10 | DMF | L6 | — | 2.0 | rt | 30 |
| 20 | $Pd(dba)_2$ | 10 | DMF | L7 | — | 2.0 | rt | 36 |
| 21 | $Pd(dba)_2$ | 10 | DMF | — | — | 2.0 | rt | 54 |
| 23 | $Pd(OAc)_2$ | 10 | DMF | L4 | — | 2.0 | rt | 55 |

TABLE 3-continued
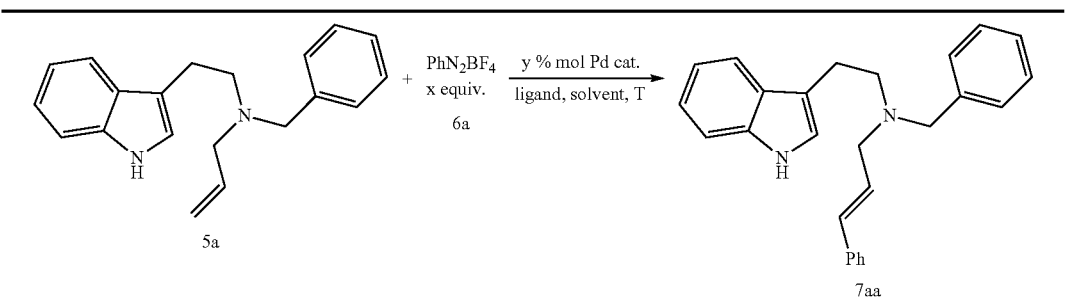
| entry | Pd cat. | y | solvent | ligand | base | x | T(° C.) | yield (%) |
|---|---|---|---|---|---|---|---|---|
| 24 | PdCl$_2$ | 10 | DMF | L4 | — | 2.0 | rt | trace |
| 25 | Pd(PPh$_3$)$_4$ | 10 | DMF | L4 | — | 2.0 | rt | trace |
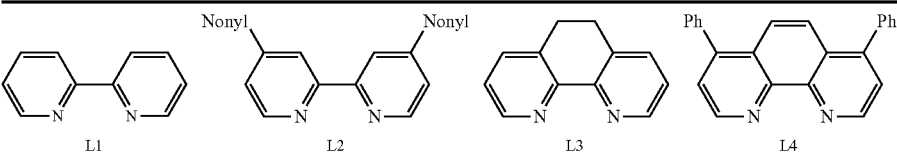
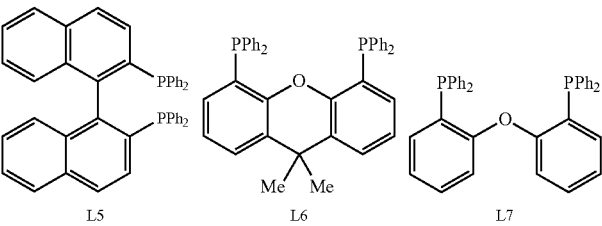
Example 64
The following compound structures were developed and tested for AC1 inhibition:
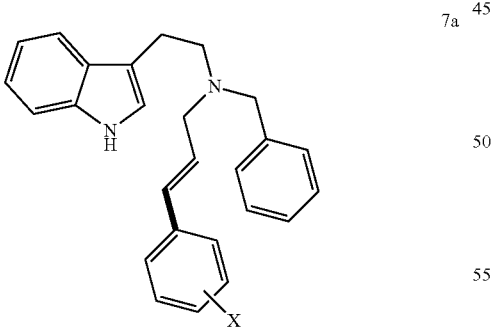
7aa: X = H
7ab: X = p-Me
7ac: X - m-Me
7ad: X = p-I
7ae: X = p-F
7af: X = p-Cl
7ag: X = p-Br
7ah: X = p-CF$_3$
7ai: X = p-CO$_2$Et
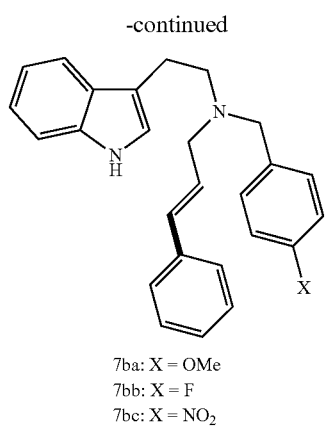
7ba: X = OMe
7bb: X = F
7bc: X = NO$_2$
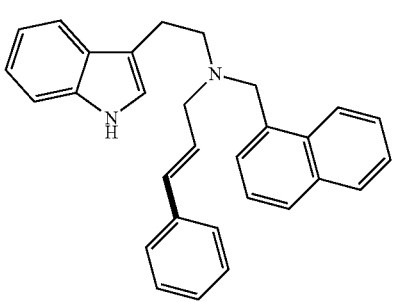

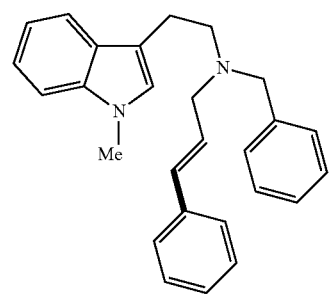
7d
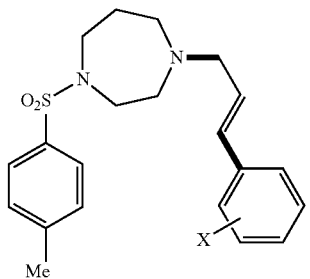
7h
7ha: X = H
7hb: X = p-Me
7hc: X = p-Cl
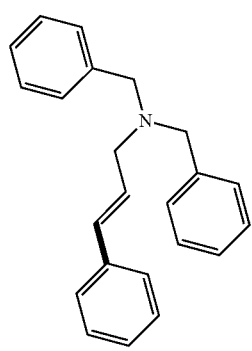
7e
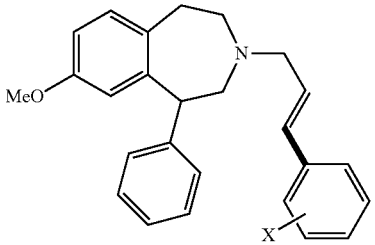
7j
7ja: X = H
7jb: X = p-Me
7jc: X = p-I
7jd: X = p-F
7je: X = p-Cl
7jf: X = p-CF₃
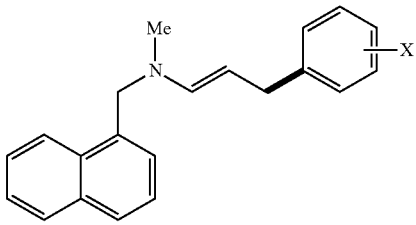
7f
7fa: X = p-Me     7fg: X = p-Br
7fb: X = m-Me     7fh: X = p-CF₃
7fc: X = o-Me     7fi: X = p-CO₂Et
7fd: X = p-I      7fj: X = p-OMe
7fe: X = p-F      7fk: X = m, p-diOMe
7ff: X = p-Cl     7fl: X = m-NO₂
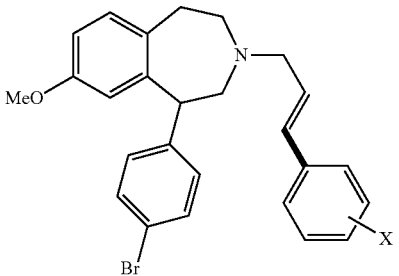
7k
7ka: X = H
7kb: X = p-Me
7kc: X = p-Cl
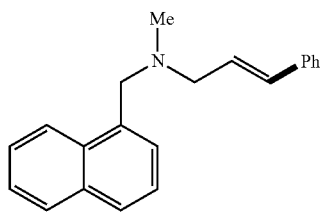
Naftifine (1)
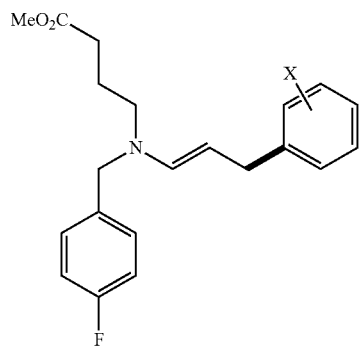
7ga: X = H
7gb: X = p-Me
7gc: X = p-Cl
7gd: X = p-CO₂E
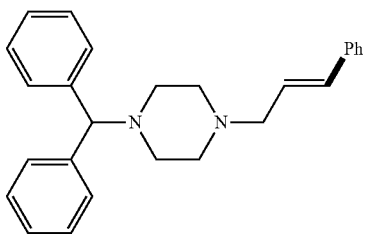
Cinarizine (2)

-continued

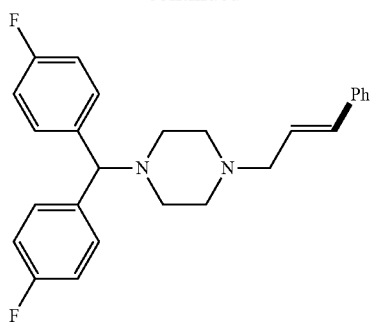

Flunarizine (3)

Table 4 shows AC1 inhibition percentages determined for the above compounds:

TABLE 4

| Compound | AC1 Inhibition Percentage | |
|---|---|---|
| | 4 μM | 40 μM |
| 7aa | 41% | 92% |
| 7ab | 20% | 91% |
| 7ac | 18% | 93% |
| 7ad | 59% | 93% |
| 7ae | 47% | 91% |
| 7af | 30% | 98% |
| 7ag | 57% | 96% |
| 7ah | 24% | 96% |
| 7ai | 36% | 99% |
| 7ba | 34% | 98% |
| 7bb | 31% | 96% |
| 7bc | 29% | 88% |
| 7c | 39% | 86% |
| 7d | −8% | 101% |
| 7e | −9% | 75% |
| 7fa | −26% | 95% |
| 7fb | 2% | 63% |
| 7fc | −71% | 77% |
| 7fd | 11% | 94% |
| 7fe | 4% | 85% |
| 7ff | 37% | 91% |
| 7fg | −61% | 93% |
| 7fh | 30% | 87% |
| 7fi | −40% | 85% |
| 7fj | −14% | 82% |
| 7fk | −14% | 33% |
| 7fl | −28% | 62% |
| 7ga | 20% | 67% |
| 7gb | −3% | 64% |
| 7gc | −24% | 70% |
| 7gd | −24% | 71% |
| 7ha | 6% | 73% |
| 7hb | −26% | 27% |
| 7hc | −5.5% | 85% |
| 7ja | 72% | 95% |
| 7jb | 43% | 90% |
| 7jc | −3% | 51% |
| 7jd | 49% | 91% |
| 7je | 33% | 78% |
| 7jf | 17% | 88% |
| 7ka | 37% | 64% |
| 7kb | 8% | 11% |
| 7kc | 32% | 32% |
| 1 | 4% | 83% |
| 2 | 22% | 89% |
| 3 | 35% | 97% |

Example 65

The AC1 inhibition for the following compounds was also tested. AC1 inhibition data (%) is listed for the two given concentrations below each compound structure:

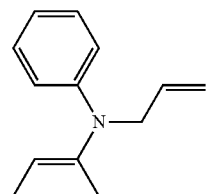

S1

40 um: 73
4 um: −17

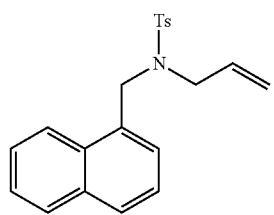

S2

40 um: 87
4 um: −28

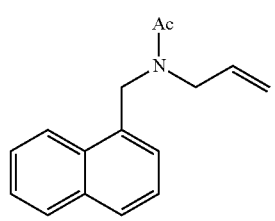

S3

40 um: −20
4 um: −12

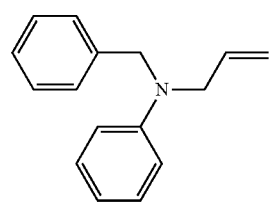

S4

40 um: 58
4 um: −17

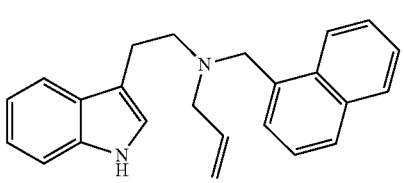

S5

40 um: 71
4 um: 3.3

S6
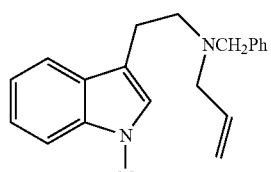
40 um: 59
4 um: -20
S7
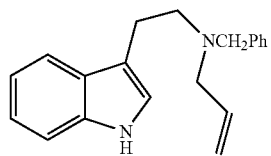
40 um: 91
4 um: -9
S8
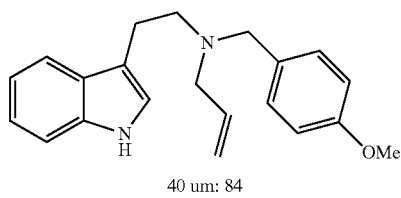
40 um: 84
4 um: 19
S9
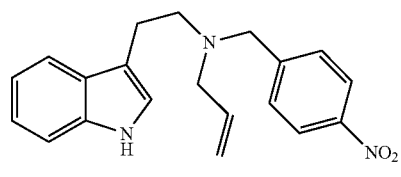
40 um: 79
4 um: -0.3
S10
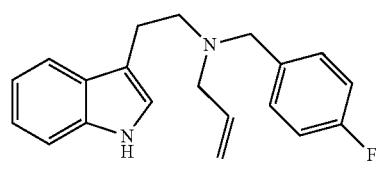
40 um: 97
4 um: -12
S11
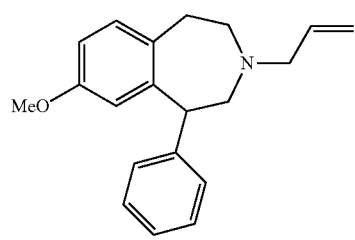
40 um: 8.6
4 um: 23
S12
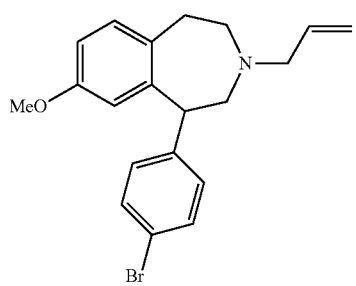
40 um: 61
4 um: -23
S13
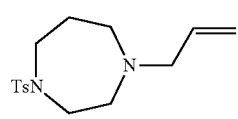
40 um: -9
4 um: 18
S14
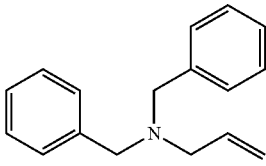
40 um: 82
4 um: -10
S15
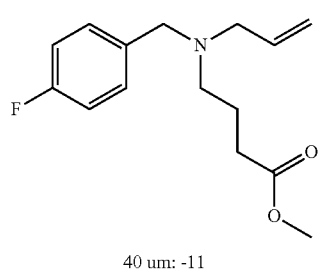
40 um: -11
4 um: 8
S16
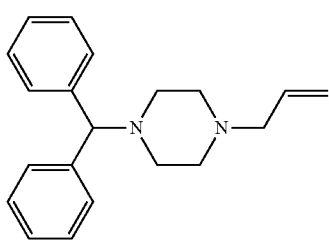
40 um: 66
4 um: 2.5

S17
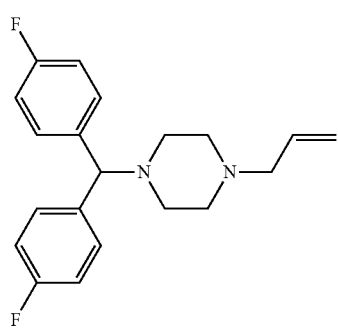
40 um: 43
4 um: 33
S18
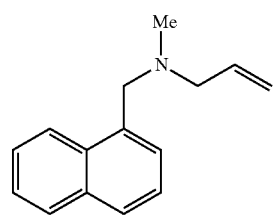
40 um: 2
4 um: -22
S19
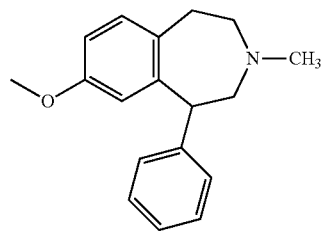
40 um: 7
4 um: 19
S20
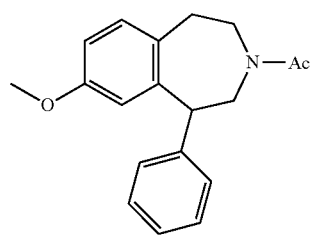
40 um: 12
4 um: -7.7
S21
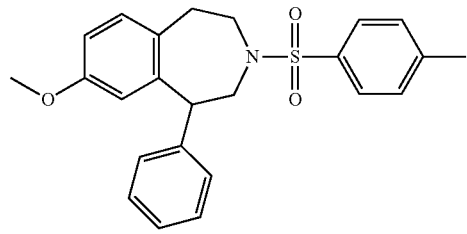
40 um: 64
4 um: 40
S22
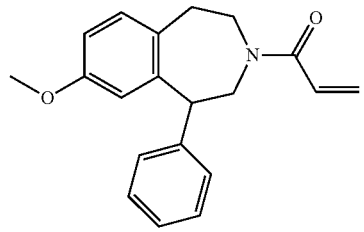
40 um: 82
4 um: 29
S23
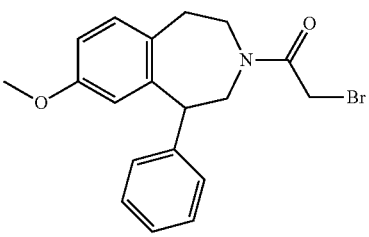
40 um: 108
4 um: 99
$IC_{50} = 0.84$ um (±0.13)
S24
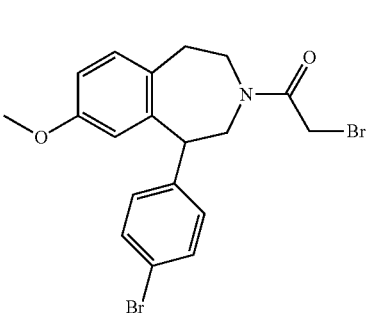
40 um: 94
4 um: 29
What is claimed is:
1. A method of inhibiting adenylyl cyclase in a patient, wherein the method comprising administering to the patient a pharmaceutical composition comprising a compound selected from the group consisting of:
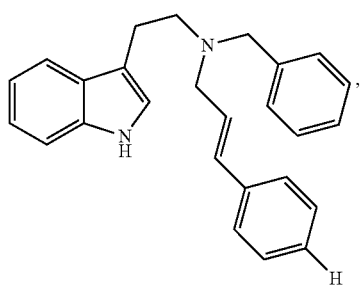

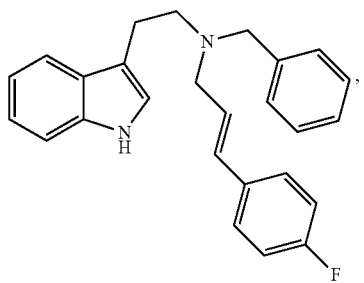

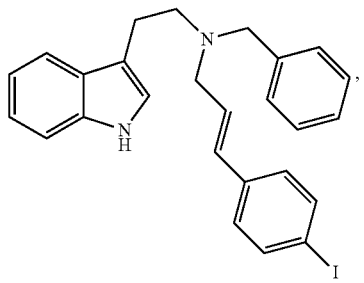

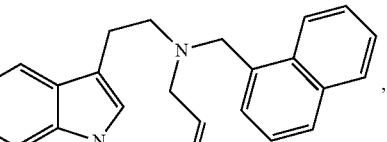

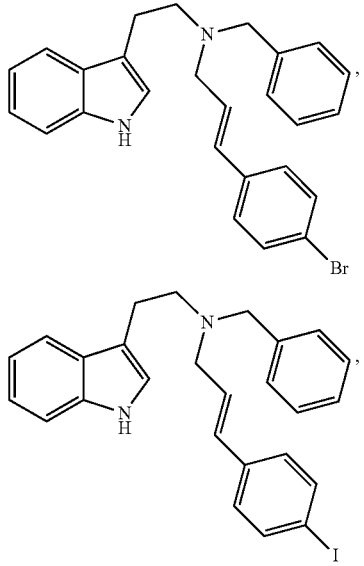

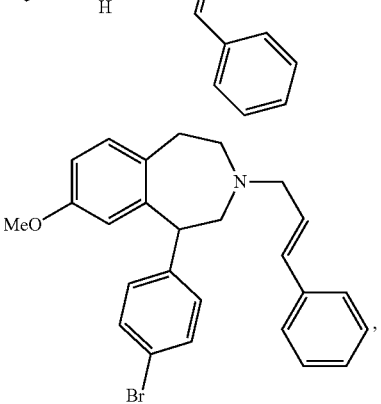

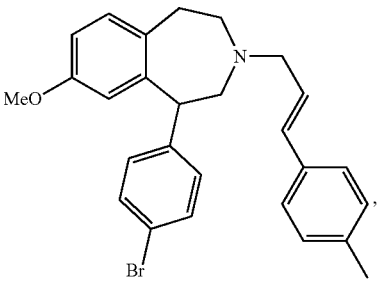

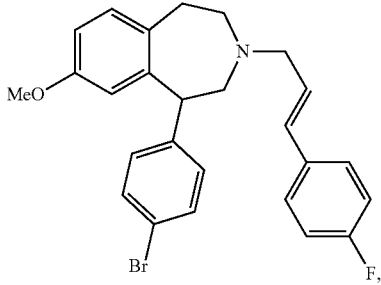

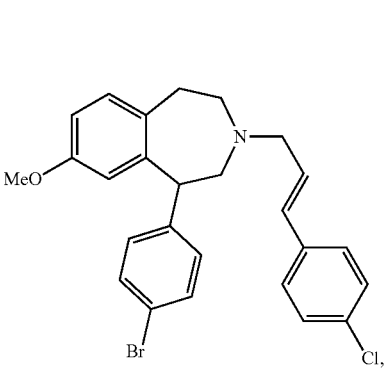

and pharmaceutically acceptable salt thereof, with a pharmaceutically acceptable carrier.

2. The method of claim 1, wherein the adenylyl cyclase is adenylyl cyclase type I (AC1).

3. A method of treating neuropathic or inflammatory pain in a patient, wherein the method comprising administering to the patient a pharmaceutical composition comprising a compound selected from the group consisting of:

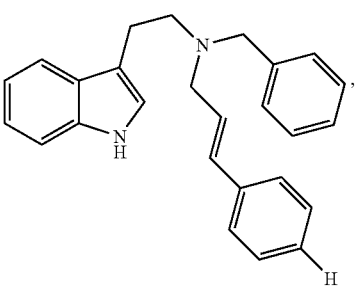

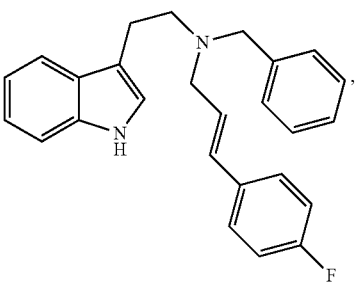

71
-continued
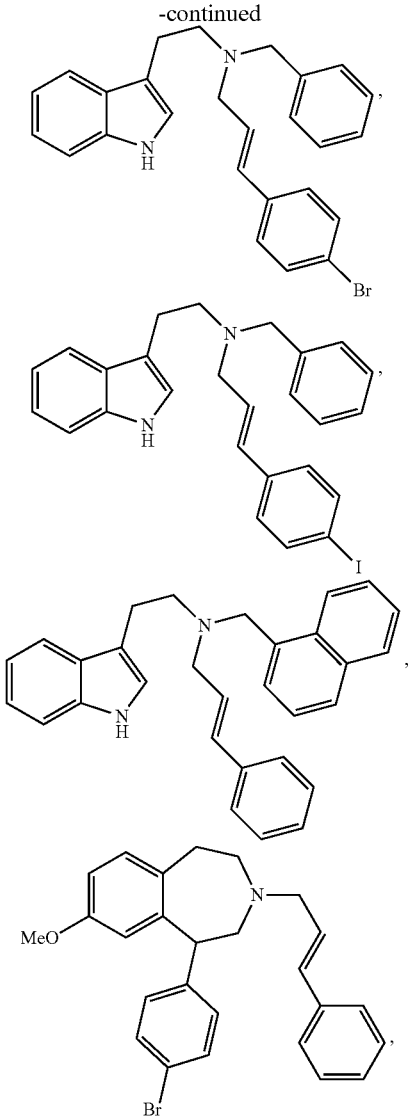
72
-continued
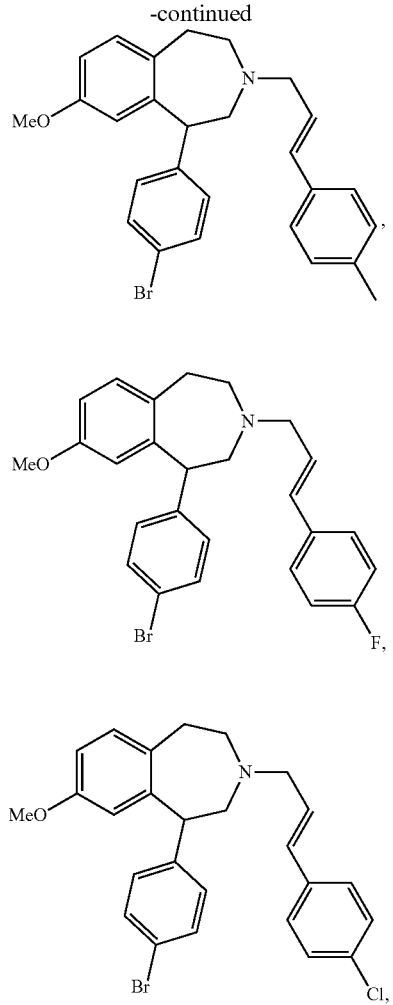
and pharmaceutically acceptable salt thereof, with a pharmaceutically acceptable carrier.
* * * * *